US012622780B2

(12) United States Patent
Gurovich

(10) Patent No.: US 12,622,780 B2
(45) Date of Patent: May 12, 2026

(54) PROSTHETIC HEART VALVE

(71) Applicant: Edwards Lifesciences Corporation, Irvine, CA (US)

(72) Inventor: Nikolai Gurovich, Hadera (IL)

(73) Assignee: Edwards Lifesciences Corporation, Irvine, CA (US)

( * ) Notice: Subject to any disclaimer, the term of this patent is extended or adjusted under 35 U.S.C. 154(b) by 632 days.

(21) Appl. No.: 17/938,786

(22) Filed: Oct. 7, 2022

(65) Prior Publication Data

US 2023/0034638 A1 Feb. 2, 2023

Related U.S. Application Data

(63) Continuation of application No. PCT/US2021/025869, filed on Apr. 6, 2021.
(Continued)

(51) Int. Cl.
*A61F 2/24* (2006.01)

(52) U.S. Cl.
CPC .... *A61F 2/2418* (2013.01); *A61F 2220/0075* (2013.01); *A61F 2230/0073* (2013.01);
(Continued)

(58) Field of Classification Search
CPC ............ A61F 2/2418; A61F 2220/0075; A61F 2230/0073; A61F 2250/0013;
(Continued)

(56) References Cited

U.S. PATENT DOCUMENTS 3,409,013 A 11/1968 Berry
3,548,417 A 12/1970 Ronnie et al.
(Continued)

FOREIGN PATENT DOCUMENTS

DE 0144167 C 9/1903
DE 2246526 A1 3/1973
(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.
(Continued)

*Primary Examiner* — Suzette J Gherbi
(74) *Attorney, Agent, or Firm* — Klarquist Sparkman LLP

(57) ABSTRACT

A prosthetic heart valve includes an expandable annular frame having an inflow end, an outflow end, an interior, an exterior, a plurality of openings, and a longitudinal axis; a plurality of commissure supports members outside of the frame; and a plurality of quadrilateral valve leaflets each having a main body having an inflow edge and an outflow edge, and a pair of opposing leaflet tabs extending from opposite sides of the main body, each leaflet tab being paired with an adjacent leaflet tab of an adjacent leaflet, each pair of leaflets tabs extending through a respective opening of the frame and coupled to one of the commissure supports to form a commissure tab assembly, wherein each commissure tab assembly is located on the exterior of the frame and the main body of each leaflet is located on the interior of the frame.

21 Claims, 14 Drawing Sheets

Related U.S. Application Data

(60) Provisional application No. 63/006,190, filed on Apr. 7, 2020.

(52) U.S. Cl.
    CPC ................. *A61F 2250/0013* (2013.01); *A61F 2250/0037* (2013.01)

(58) Field of Classification Search
    CPC ............ A61F 2250/0037; A61F 2/2415; A61F 2/2445; A61F 2/2463; A61F 2/2466
    See application file for complete search history.

(56) References Cited

U.S. PATENT DOCUMENTS

| | | | |
|---|---|---|---|
| 3,587,115 A | 6/1971 | Donald | |
| 3,657,744 A | 4/1972 | Ersek | |
| 3,671,979 A | 6/1972 | Moulopoulos | |
| 3,714,671 A | 2/1973 | Edwards et al. | |
| 3,755,823 A | 9/1973 | Hancock | |
| 4,035,849 A | 7/1977 | Angell et al. | |
| 4,056,854 A | 11/1977 | Boretos et al. | |
| 4,106,129 A | 8/1978 | Carpentier et al. | |
| 4,222,126 A | 9/1980 | Boretos et al. | |
| 4,265,694 A | 5/1981 | Boretos et al. | |
| 4,297,749 A | 11/1981 | Davis et al. | |
| RE30,912 E | 4/1982 | Hancock | |
| 4,339,831 A | 7/1982 | Johnson | |
| 4,343,048 A | 8/1982 | Ross et al. | |
| 4,345,340 A | 8/1982 | Rosen | |
| 4,373,216 A | 2/1983 | Klawitter | |
| 4,406,022 A | 9/1983 | Roy | |
| 4,441,216 A | 4/1984 | Ionescu et al. | |
| 4,470,157 A | 9/1984 | Love | |
| 4,501,030 A * | 2/1985 | Lane .................... A61F 2/2418 | |
| | | | 623/2.18 |
| 4,535,483 A | 8/1985 | Klawitter et al. | |
| 4,574,803 A | 3/1986 | Storz | |
| 4,592,340 A | 6/1986 | Boyles | |
| 4,605,407 A | 8/1986 | Black et al. | |
| 4,612,011 A | 9/1986 | Kautzky | |
| 4,643,732 A | 2/1987 | Pietsch et al. | |
| 4,655,771 A | 4/1987 | Wallsten | |
| 4,692,164 A | 9/1987 | Dzemeshkevich et al. | |
| 4,733,665 A | 3/1988 | Palmaz | |
| 4,759,758 A | 7/1988 | Gabbay | |
| 4,762,128 A | 8/1988 | Rosenbluth | |
| 4,777,951 A | 10/1988 | Cribier et al. | |
| 4,787,899 A | 11/1988 | Lazarus | |
| 4,787,901 A | 11/1988 | Baykut | |
| 4,796,629 A | 1/1989 | Grayzel | |
| 4,820,299 A | 4/1989 | Philippe et al. | |
| 4,829,990 A | 5/1989 | Thuroff et al. | |
| 4,851,001 A | 7/1989 | Taheri | |
| 4,856,516 A | 8/1989 | Hillstead | |
| 4,878,495 A | 11/1989 | Grayzel | |
| 4,878,906 A | 11/1989 | Lindemann et al. | |
| 4,883,458 A | 11/1989 | Shiber | |
| 4,922,905 A | 5/1990 | Strecker | |
| 4,966,604 A | 10/1990 | Reiss | |
| 4,979,939 A | 12/1990 | Shiber | |
| 4,986,830 A | 1/1991 | Owens et al. | |
| 4,994,077 A | 2/1991 | Dobben | |
| 5,007,896 A | 4/1991 | Shiber | |
| 5,026,366 A | 6/1991 | Leckrone | |
| 5,032,128 A | 7/1991 | Alonso | |
| 5,037,434 A | 8/1991 | Lane | |
| 5,047,041 A | 9/1991 | Samuels | |
| 5,059,177 A | 10/1991 | Towne et al. | |
| 5,080,668 A | 1/1992 | Bolz et al. | |
| 5,085,635 A | 2/1992 | Cragg | |
| 5,089,015 A | 2/1992 | Ross | |
| 5,152,771 A | 10/1992 | Sabbaghian et al. | |
| 5,163,953 A | 11/1992 | Vince | |
| 5,167,628 A | 12/1992 | Boyles | |
| 5,192,297 A | 3/1993 | Hull | |
| 5,266,073 A | 11/1993 | Wall | |
| 5,282,847 A | 2/1994 | Trescony et al. | |
| 5,295,958 A | 3/1994 | Shturman | |
| 5,332,402 A | 7/1994 | Teitelbaum | |
| 5,360,444 A | 11/1994 | Kusuhara | |
| 5,370,685 A | 12/1994 | Stevens | |
| 5,397,351 A | 3/1995 | Pavcnik et al. | |
| 5,411,055 A | 5/1995 | Kane | |
| 5,411,552 A | 5/1995 | Andersen et al. | |
| 5,443,446 A | 8/1995 | Shturman | |
| 5,480,424 A | 1/1996 | Cox | |
| 5,500,014 A | 3/1996 | Quijano et al. | |
| 5,545,209 A | 8/1996 | Roberts et al. | |
| 5,545,214 A | 8/1996 | Stevens | |
| 5,549,665 A | 8/1996 | Vesely et al. | |
| 5,554,185 A | 9/1996 | Block et al. | |
| 5,558,644 A | 9/1996 | Boyd et al. | |
| 5,571,175 A | 11/1996 | Vanney et al. | |
| 5,584,803 A | 12/1996 | Stevens et al. | |
| 5,591,185 A | 1/1997 | Kilmer et al. | |
| 5,591,195 A | 1/1997 | Taheri et al. | |
| 5,607,464 A | 3/1997 | Trescony et al. | |
| 5,609,626 A | 3/1997 | Quijano et al. | |
| 5,628,792 A | 5/1997 | Lentell | |
| 5,639,274 A | 6/1997 | Fischell et al. | |
| 5,665,115 A | 9/1997 | Cragg | |
| 5,716,417 A | 2/1998 | Girard et al. | |
| 5,728,068 A | 3/1998 | Leone et al. | |
| 5,749,890 A | 5/1998 | Shaknovich | |
| 5,756,476 A | 5/1998 | Epstein et al. | |
| 5,769,812 A | 6/1998 | Stevens et al. | |
| 5,800,508 A | 9/1998 | Goicoechea et al. | |
| 5,840,081 A | 11/1998 | Andersen et al. | |
| 5,855,597 A | 1/1999 | Jayaraman | |
| 5,855,601 A | 1/1999 | Bessler et al. | |
| 5,855,602 A | 1/1999 | Angell | |
| 5,910,170 A * | 6/1999 | Reimink .............. A61F 2/2418 | |
| | | | 623/2.38 |
| 5,925,063 A | 7/1999 | Khosravi | |
| 5,957,949 A | 9/1999 | Leonhardt et al. | |
| 6,027,525 A | 2/2000 | Suh et al. | |
| 6,132,473 A | 10/2000 | Williams et al. | |
| 6,168,614 B1 | 1/2001 | Andersen et al. | |
| 6,171,335 B1 | 1/2001 | Wheatley et al. | |
| 6,174,327 B1 | 1/2001 | Mertens et al. | |
| 6,210,408 B1 | 4/2001 | Chandrasekaran et al. | |
| 6,217,585 B1 | 4/2001 | Houser et al. | |
| 6,221,091 B1 | 4/2001 | Khosravi | |
| 6,231,602 B1 | 5/2001 | Carpentier et al. | |
| 6,245,102 B1 | 6/2001 | Jayaraman | |
| 6,299,637 B1 | 10/2001 | Shaolian et al. | |
| 6,302,906 B1 | 10/2001 | Goicoechea et al. | |
| 6,338,740 B1 | 1/2002 | Carpentier | |
| 6,350,277 B1 | 2/2002 | Kocur | |
| 6,352,547 B1 | 3/2002 | Brown et al. | |
| 6,425,916 B1 | 7/2002 | Garrison et al. | |
| 6,440,764 B1 | 8/2002 | Focht et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,468,660 B2 | 10/2002 | Ogle et al. | |
| 6,482,228 B1 | 11/2002 | Norred | |
| 6,488,704 B1 | 12/2002 | Connelly et al. | |
| 6,527,979 B2 | 3/2003 | Constantz et al. | |
| 6,569,196 B1 | 5/2003 | Vesely | |
| 6,582,462 B1 | 6/2003 | Andersen et al. | |
| 6,605,112 B1 | 8/2003 | Moll et al. | |
| 6,652,578 B2 | 11/2003 | Bailey et al. | |
| 6,689,123 B2 | 2/2004 | Pinchasik | |
| 6,716,244 B2 | 4/2004 | Klaco | |
| 6,730,118 B2 | 5/2004 | Spenser et al. | |
| 6,733,525 B2 | 5/2004 | Yang et al. | |
| 6,767,362 B2 * | 7/2004 | Schreck ................ A61F 2/2427 | |
| | | | 623/2.14 |
| 6,769,161 B2 | 8/2004 | Brown et al. | |
| 6,783,542 B2 | 8/2004 | Eidenschink | |
| 6,830,584 B1 | 12/2004 | Seguin | |
| 6,878,162 B2 | 4/2005 | Bales et al. | |

(56) References Cited

U.S. PATENT DOCUMENTS

| | | | |
|---|---|---|---|
| 6,893,460 B2 | 5/2005 | Spenser et al. | |
| 6,908,481 B2 | 6/2005 | Cribier | |
| 6,936,067 B2 | 8/2005 | Buchanan | |
| 7,018,406 B2 | 3/2006 | Seguin et al. | |
| 7,018,408 B2 | 3/2006 | Bailey et al. | |
| 7,096,554 B2 | 8/2006 | Austin et al. | |
| 7,225,518 B2 | 6/2007 | Eidenschink et al. | |
| 7,276,078 B2 | 10/2007 | Spenser et al. | |
| 7,276,084 B2 | 10/2007 | Yang et al. | |
| 7,316,710 B1 | 1/2008 | Cheng et al. | |
| 7,318,278 B2 | 1/2008 | Zhang et al. | |
| 7,374,571 B2 | 5/2008 | Pease et al. | |
| 7,393,360 B2 | 7/2008 | Spenser et al. | |
| 7,462,191 B2 | 12/2008 | Spenser et al. | |
| 7,510,575 B2 | 3/2009 | Spenser et al. | |
| 7,563,280 B2 | 7/2009 | Anderson et al. | |
| 7,585,321 B2 | 9/2009 | Cribier | |
| 7,618,446 B2 | 11/2009 | Andersen et al. | |
| 7,618,447 B2 | 11/2009 | Case et al. | |
| 7,655,034 B2 | 2/2010 | Mitchell et al. | |
| 7,785,366 B2 | 8/2010 | Maurer et al. | |
| 7,959,665 B2 | 6/2011 | Pienknagura | |
| 7,959,672 B2 | 6/2011 | Salahieh et al. | |
| 7,993,394 B2 | 8/2011 | Hariton et al. | |
| 8,029,556 B2 | 10/2011 | Rowe | |
| 8,075,611 B2 | 12/2011 | Millwee et al. | |
| 8,128,686 B2 | 3/2012 | Paul et al. | |
| 8,167,932 B2 | 5/2012 | Bourang et al. | |
| 8,291,570 B2 | 10/2012 | Eidenschink et al. | |
| 8,348,998 B2 | 1/2013 | Pintor et al. | |
| 8,449,606 B2 | 5/2013 | Eliasen et al. | |
| 8,454,685 B2 | 6/2013 | Hariton et al. | |
| 8,652,203 B2 | 2/2014 | Quadri et al. | |
| 8,685,055 B2 | 4/2014 | VanTassel et al. | |
| 8,747,463 B2 | 6/2014 | Fogarty et al. | |
| 9,078,781 B2 | 7/2015 | Ryan et al. | |
| 9,393,110 B2 * | 7/2016 | Levi | A61F 2/2418 |
| 11,090,158 B2 * | 8/2021 | Noe | A61F 2/2409 |
| 11,224,509 B2 | 1/2022 | Dasi et al. | |
| 2001/0021872 A1 | 9/2001 | Bailey et al. | |
| 2002/0026094 A1 | 2/2002 | Roth | |
| 2002/0032481 A1 | 3/2002 | Gabbay | |
| 2002/0138135 A1 | 9/2002 | Duerig et al. | |
| 2002/0143390 A1 | 10/2002 | Ishii | |
| 2002/0173842 A1 | 11/2002 | Buchanan | |
| 2003/0014105 A1 | 1/2003 | Cao | |
| 2003/0040791 A1 | 2/2003 | Oktay | |
| 2003/0050694 A1 | 3/2003 | Yang et al. | |
| 2003/0100939 A1 | 5/2003 | Yodfat et al. | |
| 2003/0158597 A1 | 8/2003 | Quiachon et al. | |
| 2003/0212454 A1 | 11/2003 | Scott et al. | |
| 2004/0024452 A1 | 2/2004 | Kruse et al. | |
| 2004/0039436 A1 | 2/2004 | Spenser et al. | |
| 2004/0078074 A1 | 4/2004 | Anderson et al. | |
| 2004/0186558 A1 | 9/2004 | Pavcnik et al. | |
| 2004/0186563 A1 | 9/2004 | Lobbi | |
| 2004/0186565 A1 | 9/2004 | Schreck | |
| 2004/0260389 A1 | 12/2004 | Case et al. | |
| 2005/0010285 A1 | 1/2005 | Lambrecht et al. | |
| 2005/0075725 A1 | 4/2005 | Rowe | |
| 2005/0075728 A1 | 4/2005 | Nguyen et al. | |
| 2005/0096736 A1 | 5/2005 | Osse et al. | |
| 2005/0096738 A1 | 5/2005 | Cali et al. | |
| 2005/0137686 A1 | 6/2005 | Salahieh et al. | |
| 2005/0188525 A1 | 9/2005 | Weber et al. | |
| 2005/0203614 A1 | 9/2005 | Forster et al. | |
| 2005/0203617 A1 | 9/2005 | Forster et al. | |
| 2005/0234546 A1 | 10/2005 | Nugent et al. | |
| 2006/0004469 A1 | 1/2006 | Sokel | |
| 2006/0025857 A1 | 2/2006 | Bergheim et al. | |
| 2006/0058872 A1 | 3/2006 | Salahieh et al. | |
| 2006/0074484 A1 | 4/2006 | Huber | |
| 2006/0108090 A1 | 5/2006 | Ederer et al. | |
| 2006/0149350 A1 | 7/2006 | Patel et al. | |
| 2006/0183383 A1 | 8/2006 | Asmus et al. | |
| 2006/0229719 A1 | 10/2006 | Marquez et al. | |
| 2006/0259136 A1 | 11/2006 | Nguyen et al. | |
| 2006/0259137 A1 | 11/2006 | Artof et al. | |
| 2006/0287717 A1 | 12/2006 | Rowe et al. | |
| 2007/0005131 A1 | 1/2007 | Taylor | |
| 2007/0010876 A1 | 1/2007 | Salahieh et al. | |
| 2007/0010877 A1 | 1/2007 | Salahieh et al. | |
| 2007/0112422 A1 | 5/2007 | Dehdashtian | |
| 2007/0162102 A1 | 7/2007 | Ryan et al. | |
| 2007/0203503 A1 | 8/2007 | Salahieh et al. | |
| 2007/0203575 A1 | 8/2007 | Forster et al. | |
| 2007/0203576 A1 | 8/2007 | Lee et al. | |
| 2007/0208550 A1 * | 9/2007 | Cao | G06F 30/23 |
| | | | 703/11 |
| 2007/0213813 A1 | 9/2007 | Segesser et al. | |
| 2007/0233228 A1 | 10/2007 | Eberhardt et al. | |
| 2007/0260305 A1 | 11/2007 | Drews et al. | |
| 2007/0265700 A1 | 11/2007 | Eliasen et al. | |
| 2008/0021546 A1 | 1/2008 | Patz et al. | |
| 2008/0114442 A1 | 5/2008 | Mitchell et al. | |
| 2008/0125853 A1 | 5/2008 | Bailey et al. | |
| 2008/0154355 A1 | 6/2008 | Benichou et al. | |
| 2008/0183271 A1 | 7/2008 | Frawley et al. | |
| 2008/0208327 A1 | 8/2008 | Rowe | |
| 2008/0243245 A1 | 10/2008 | Thambar et al. | |
| 2008/0255660 A1 | 10/2008 | Guyenot et al. | |
| 2008/0275537 A1 | 11/2008 | Limon | |
| 2008/0294248 A1 | 11/2008 | Yang et al. | |
| 2009/0118826 A1 | 5/2009 | Khaghani | |
| 2009/0125118 A1 | 5/2009 | Gong | |
| 2009/0157175 A1 | 6/2009 | Benichou | |
| 2009/0276040 A1 | 11/2009 | Rowe et al. | |
| 2009/0281619 A1 | 11/2009 | Le et al. | |
| 2009/0287296 A1 | 11/2009 | Manasse | |
| 2009/0287299 A1 | 11/2009 | Tabor et al. | |
| 2009/0292350 A1 | 11/2009 | Eberhardt et al. | |
| 2009/0299452 A1 | 12/2009 | Eidenschink et al. | |
| 2009/0319037 A1 | 12/2009 | Rowe et al. | |
| 2010/0004735 A1 | 1/2010 | Yang et al. | |
| 2010/0049313 A1 | 2/2010 | Alon et al. | |
| 2010/0082094 A1 | 4/2010 | Quadri et al. | |
| 2010/0100176 A1 | 4/2010 | Elizondo et al. | |
| 2010/0168844 A1 | 7/2010 | Toomes et al. | |
| 2010/0185277 A1 | 7/2010 | Braido et al. | |
| 2010/0198347 A1 | 8/2010 | Zakay et al. | |
| 2010/0204781 A1 | 8/2010 | Alkhatib | |
| 2011/0015729 A1 | 1/2011 | Jimenez et al. | |
| 2011/0022157 A1 | 1/2011 | Essinger et al. | |
| 2011/0066224 A1 | 3/2011 | White | |
| 2011/0137397 A1 | 6/2011 | Chau et al. | |
| 2011/0218619 A1 | 9/2011 | Benichou et al. | |
| 2011/0319991 A1 | 12/2011 | Hariton et al. | |
| 2012/0030090 A1 | 2/2012 | Johnston et al. | |
| 2012/0089223 A1 | 4/2012 | Nguyen et al. | |
| 2012/0101571 A1 | 4/2012 | Thambar et al. | |
| 2012/0123529 A1 | 5/2012 | Levi et al. | |
| 2012/0259409 A1 | 10/2012 | Nguyen et al. | |
| 2013/0023984 A1 * | 1/2013 | Conklin | A61F 2/2418 |
| | | | 623/2.14 |
| 2013/0023985 A1 | 1/2013 | Khairkhahan et al. | |
| 2013/0046373 A1 | 2/2013 | Cartledge et al. | |
| 2013/0150956 A1 | 6/2013 | Yohanan et al. | |
| 2013/0166017 A1 | 6/2013 | Cartledge et al. | |
| 2013/0190857 A1 | 7/2013 | Mitra et al. | |
| 2013/0274873 A1 | 10/2013 | Delaloye et al. | |
| 2013/0310926 A1 | 11/2013 | Hariton | |
| 2013/0317598 A1 | 11/2013 | Rowe et al. | |
| 2013/0331929 A1 | 12/2013 | Mitra et al. | |
| 2014/0194981 A1 | 7/2014 | Menk et al. | |
| 2014/0200661 A1 | 7/2014 | Pintor et al. | |
| 2014/0209238 A1 | 7/2014 | Bonyuet et al. | |
| 2014/0222136 A1 | 8/2014 | Geist et al. | |
| 2014/0277417 A1 | 9/2014 | Schraut et al. | |
| 2014/0277419 A1 | 9/2014 | Garde et al. | |
| 2014/0277424 A1 | 9/2014 | Oslund | |
| 2014/0277563 A1 | 9/2014 | White | |
| 2014/0296962 A1 | 10/2014 | Cartledge et al. | |
| 2014/0330372 A1 | 11/2014 | Weston et al. | |
| 2014/0343670 A1 | 11/2014 | Bakis et al. | |

(56) References Cited

U.S. PATENT DOCUMENTS

| | | | |
|---|---|---|---|
| 2014/0343671 A1 | 11/2014 | Yohanan et al. | |
| 2014/0350667 A1 | 11/2014 | Braido et al. | |
| 2015/0073545 A1 | 3/2015 | Braido | |
| 2015/0073546 A1 | 3/2015 | Braido | |
| 2015/0135506 A1 | 5/2015 | White | |
| 2015/0157455 A1 | 6/2015 | Hoang et al. | |
| 2016/0374802 A1* | 12/2016 | Levi | A61F 2/2418 |
| | | | 623/2.14 |
| 2017/0014229 A1 | 1/2017 | Nguyen-Thien-Nhon et al. | |
| 2018/0008405 A1 | 1/2018 | Girard et al. | |
| 2018/0028310 A1 | 2/2018 | Gurovich et al. | |
| 2018/0153689 A1 | 6/2018 | Maimon et al. | |
| 2018/0325665 A1 | 11/2018 | Gurovich et al. | |
| 2018/0344456 A1 | 12/2018 | Barash et al. | |
| 2019/0159894 A1 | 5/2019 | Levi et al. | |
| 2019/0192288 A1 | 6/2019 | Levi et al. | |
| 2019/0192289 A1 | 6/2019 | Levi et al. | |
| 2019/0328525 A1* | 10/2019 | Noe | A61F 2/2412 |
| 2020/0069420 A1* | 3/2020 | Levi | A61F 2/2418 |
| 2023/0034638 A1* | 2/2023 | Gurovich | A61F 2/2415 |
| 2025/0228664 A1* | 7/2025 | Noe | A61F 2/2445 |

FOREIGN PATENT DOCUMENTS

| | | | |
|---|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0103546 B1 | 5/1988 |
| EP | 0850607 A1 | 7/1998 |
| EP | 1057460 A1 | 12/2000 |
| EP | 1088529 A2 | 4/2001 |
| EP | 1570809 A1 | 9/2005 |
| FR | 2788217 A1 | 7/2000 |
| FR | 2815844 A1 | 5/2002 |
| GB | 2056023 A | 3/1981 |
| JP | 2020505980 A | 2/2020 |
| SU | 1271508 A1 | 11/1986 |
| WO | 9117720 A1 | 11/1991 |
| WO | 1991017720 A1 | 11/1991 |
| WO | 9217118 A1 | 10/1992 |
| WO | 1992017118 A1 | 10/1992 |
| WO | 9301768 A1 | 2/1993 |
| WO | 1993001768 A1 | 2/1993 |
| WO | 9724080 A1 | 7/1997 |
| WO | 1997024080 A1 | 7/1997 |
| WO | 9829057 A1 | 7/1998 |
| WO | 1998029057 A1 | 7/1998 |
| WO | 9930646 A1 | 6/1999 |
| WO | 1999030646 A1 | 6/1999 |
| WO | 9933414 A1 | 7/1999 |
| WO | 1999033414 A1 | 7/1999 |
| WO | 9940964 A1 | 8/1999 |
| WO | 1999040964 A1 | 8/1999 |
| WO | 9947075 A1 | 9/1999 |
| WO | 1999047075 A1 | 9/1999 |
| WO | 0018333 A1 | 4/2000 |
| WO | 2000018333 A1 | 4/2000 |
| WO | 0041652 A1 | 7/2000 |
| WO | 2000041652 A1 | 7/2000 |
| WO | 2000047139 A1 | 8/2000 |
| WO | 0135878 A2 | 5/2001 |
| WO | 2001035878 A2 | 5/2001 |
| WO | 0149213 A2 | 7/2001 |
| WO | 2001049213 A2 | 7/2001 |
| WO | 0154624 A1 | 8/2001 |
| WO | 0154625 A1 | 8/2001 |
| WO | 0162189 A1 | 8/2001 |
| WO | 2001054624 A1 | 8/2001 |
| WO | 2001054625 A1 | 8/2001 |
| WO | 2001062189 A1 | 8/2001 |
| WO | 0047139 A9 | 9/2001 |
| WO | 0164137 A1 | 9/2001 |
| WO | 2001064137 A1 | 9/2001 |
| WO | 0176510 A2 | 10/2001 |
| WO | 2001076510 A2 | 10/2001 |
| WO | 0222054 | 3/2002 |
| WO | 2002022054 A1 | 3/2002 |
| WO | 0236048 A1 | 5/2002 |
| WO | 0241789 A2 | 5/2002 |
| WO | 2002036048 A1 | 5/2002 |
| WO | 2002041789 A2 | 5/2002 |
| WO | 0243620 A1 | 6/2002 |
| WO | 0247575 A2 | 6/2002 |
| WO | 0249540 A2 | 6/2002 |
| WO | 2002043620 A1 | 6/2002 |
| WO | 2002047575 A2 | 6/2002 |
| WO | 2002049540 A2 | 6/2002 |
| WO | 03047468 | 6/2003 |
| WO | 2003047468 A1 | 6/2003 |
| WO | 2005034812 A1 | 4/2005 |
| WO | 2005055883 A1 | 6/2005 |
| WO | 2005084595 A1 | 9/2005 |
| WO | 2005102015 A1 | 11/2005 |
| WO | 2006014233 A2 | 2/2006 |
| WO | 2006032051 A2 | 3/2006 |
| WO | 2006034008 A2 | 3/2006 |
| WO | 2006111391 A1 | 10/2006 |
| WO | 2006127089 A1 | 11/2006 |
| WO | 2006138173 A2 | 12/2006 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008035337 A2 | 3/2008 |
| WO | 2008091515 A2 | 7/2008 |
| WO | 2008147964 A1 | 12/2008 |
| WO | 2008150529 A1 | 12/2008 |
| WO | 2009033469 A1 | 3/2009 |
| WO | 2009042196 A2 | 4/2009 |
| WO | 2009053497 A1 | 4/2009 |
| WO | 2009061389 A2 | 5/2009 |
| WO | 2009094188 A2 | 7/2009 |
| WO | 2009116041 A2 | 9/2009 |
| WO | 2009149462 A2 | 12/2009 |
| WO | 2010011699 A2 | 1/2010 |
| WO | 2010121076 A2 | 10/2010 |
| WO | 2013106585 A1 | 7/2013 |
| WO | 2015085218 A1 | 6/2015 |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

Walther T, Dehdashtian MM, Khanna R, Young E, Goldbrunner PJ, Lee W. Trans-catheter valve-in-valve implantation: in vitro hydro-

(56)     References Cited

OTHER PUBLICATIONS dynamic performance of the Sapien+cloth trans-catheter heart valve in the Carpentier-Edwards Perimount valves. Eur J Cardiothorac Surg. 2011;40(5):1120-6. Epub Apr. 7, 2011.

Fontaine, M.D., Arthur B., et al, "Vascular Stent Prototype; Results of Preclinical Evaluation", p. 29-34; Technical Developments and Instrumentation; Jan.-Feb. 1996, vol. 7, No. 1.

Fontaine, M.D., Arthur B., et al, "Prototype Stent: Invivo Swine Studies in the Biliary System", p. 101-105, Journal of Vascular and Interventional Radiology; Jan.-Feb. 1997; vol. 8, No. 1.

Patrick W. Serruys, Nicolo Piazza, Alain Cribier, John Webb, Jean-Claude Laborde, Peter de Jaegere, "Transcatheter Aortic Valve Implantation: Tips and Tricks to Avoid Failure"; we file the table of contents and pp. 18 to 39 (Chapter 2) and pp. 102-114 (Chapter 8); the publication date according to the "Library of Congress Cataloging-in-Publication Data" is Nov. 24, 2009.

Fontaine, M.D., Arthur B., et al, "Prototype Stent: Invivo Swine Studies in the Biliary System1", p. 101-105, Journal of Vascular and Interventional Radiology; Jan.-Feb. 1997; vol. 8, No. 1.

* cited by examiner

PROSTHETIC HEART VALVE

CROSS-REFERENCED TO RELATED APPLICATION

The present application is a continuation of PCT patent application no. PCT/US2021/025869, filed Apr. 6, 2021, which application claims the benefit of U.S. Provisional Application No. 63/006,190, filed Apr. 7, 2020, each of which is incorporated herein in its entirety by this specific reference.

FIELD

The present disclosure relates to prosthetic heart valves, and to methods and assemblies for forming leaflet assemblies and attaching leaflet assemblies to a frame of such prosthetic heart valves.

BACKGROUND

The human heart can suffer from various valvular diseases. These valvular diseases can result in significant malfunctioning of the heart and ultimately require repair of the native valve or replacement of the native valve with an artificial valve. There are a number of known repair devices (e.g., stents) and artificial valves, as well as a number of known methods of implanting these devices and valves in humans. Percutaneous and minimally-invasive surgical approaches are used in various procedures to deliver prosthetic medical devices to locations inside the body that are not readily accessible by surgery or where access without surgery is desirable. In one specific example, a prosthetic heart valve can be mounted in a crimped state on the distal end of a delivery apparatus and advanced through the patient's vasculature (e.g., through a femoral artery and the aorta) until the prosthetic heart valve reaches the implantation site in the heart. The prosthetic heart valve is then expanded to its functional size, for example, by inflating a balloon on which the prosthetic valve is mounted, actuating a mechanical actuator that applies an expansion force to the prosthetic heart valve, or by deploying the prosthetic heart valve from a sheath of the delivery apparatus so that the prosthetic heart valve can self-expand to its functional size.

Most expandable, transcatheter heart valves are used for mid to high expansion diameters, for example diameters ranging from 23 to 29 mm. While smaller prosthetic valves available, such as those with diameters of about 20 mm or less, smaller diameter valves are rarely used due to a variety of challenges. For example, smaller diameter prosthetic valves generally cause higher pressure gradients along the prosthetic valve, which can lead to various clinical risks, such as cavitation. Also, smaller prosthetic valves typically have shorter paravalvular sealing elements, which makes it more challenging for the clinician to align the prosthetic valve at the native annulus. Smaller prosthetic valves also can have relatively shorter frames, which can result in leaflet overhang, in which the native valve leaflets overhang the outflow end of the prosthetic valve, thereby disturbing blood flow and/or inhibiting full opening of the prosthetic leaflets. Further, smaller prosthetic valves have relatively smaller frame openings, which can inhibit coronary access through the frame with a catheter in a subsequent procedure. Finally, valve-in-valve procedures involving implantation of a second prosthetic valve in a previously implanted prosthetic valve is more challenging with relatively smaller prosthetic valves because it is more difficult to properly align and orient the second prosthetic valve within the previously implanted prosthetic valve while maintaining access to the coronary ostia.

Accordingly, a need exists for improved prosthetic heart valve leaflet assemblies and methods for assembling the leaflet assemblies to a frame of the prosthetic heart valve.

SUMMARY

Described herein are embodiments of methods for assembling a prosthetic heart valve including a leaflet assembly, methods of assembling a leaflet sub-assembly of the leaflet assembly, and prosthetic heart valves including a leaflet assembly.

In one representative embodiment, a prosthetic heart valve is provided. The prosthetic heart valve includes an expandable annular frame, a plurality of commissure support members outside of the frame, and a plurality of quadrilateral valve leaflets. The expandable annular frame has an inflow end, an outflow end, an interior, an exterior, a plurality of openings, and a longitudinal axis. Each of the plurality of quadrilateral valve leaflets have a main body having an inflow edge and an outflow edge, and a pair of opposing leaflet tabs extending from opposite sides of the main body, each leaflet tab being paired with an adjacent leaflet tab of an adjacent leaflet, each pair of leaflets tabs extending through a respective opening of the frame and coupled to one of the commissure supports to form a commissure tab assembly, wherein each commissure tab assembly is located on the exterior of the frame and the main body of each leaflet is located on the interior of the frame. The inflow edges of the leaflets and the inflow end of the frame are aligned, and the outflow edges of the leaflets are axially offset from the outflow end of the frame along the longitudinal axis.

In another representative embodiment, a prosthetic heart valve includes an annular frame having an inflow end, an outflow end, a plurality of openings, and a longitudinal axis; a plurality of commis sure support members each having an outer surface and an inner surface; and a plurality of valve leaflets each having a main body having an inflow edge and an outflow edge, and a pair of opposing leaflet tabs extending from opposite sides of the main body. Each leaflet tab is paired with an adjacent leaflet tab of an adjacent leaflet, wherein each pair of leaflets tabs extends through a respective opening of the frame and is coupled to one of the commis sure supports outside of the frame to form a commissure tab assembly. Each leaflet tab forms a first fold extending radially outwardly from the main body of a respective leaflet through a respective opening of the frame, a second fold extending circumferentially between the inner surface of a respective support member and an exterior surface of the frame, and a third fold extending circumferentially along the outer surface of the support member.

In another representative embodiment, a prosthetic heart valve includes an expandable annular frame having an inflow end, an outflow end, an interior, an exterior, a plurality of openings, and a longitudinal axis; a plurality of commis sure supports members outside of the frame; and a plurality of valve leaflets each having a main body having an inflow edge and an outflow edge, and a pair of opposing leaflet tabs extending from opposite sides of the main body. Each leaflet tab being paired with an adjacent leaflet tab of an adjacent leaflet, each pair of leaflets tabs extending through a respective opening of the frame and coupled to one of the commis sure supports to form a commis sure tab assembly, wherein each commissure tab assembly is located on the exterior of the frame and the main body of each leaflet is located on the interior of the frame. For each commis sure tab assembly, the commis sure support member has a height that is greater than a height of a respective frame opening through which the pair of leaflet tabs extends.

In another representative embodiments, a leaflet assembly for a prosthetic heart valve includes a plurality of valve leaflets and a plurality of commis sure support members. Each leaflet includes a main body having an inflow edge and an outflow edge and opposing commissure tabs extending from opposite sides of the main body. Each commissure support member has a pair of opposing faces. Each commissure tab is paired with an adjacent commissure tab of an adjacent leaflet and for each pair of commissure tabs, the commissure tabs are wrapped partially around and coupled to the opposing faces of one of the support members to form a commissure assembly.

In another representative embodiment, a method for assembling a prosthetic heart valve is provided. The method includes forming a leaflet assembly from a plurality of leaflets, each leaflet comprising opposing commissure tabs, wherein the leaflet assembly is formed by pairing a commissure tab of each leaflet with an adjacent commissure tab of an adjacent leaflet and connecting each pair of commissure tabs to a commissure support member to form a respective commissure assembly of the leaflet assembly. The method further includes positioning the leaflet assembly within an interior of an expandable annular frame, wherein the frame defines a plurality of openings; and inserting each of the commis sure assemblies through a respective opening of the frame so as to position the commis sure assemblies an exterior of the frame.

The foregoing and other objects, features, and advantages of the invention will become more apparent from the following detailed description, which proceeds with reference to the accompanying figures.

DETAILED DESCRIPTION

Described herein are examples of prosthetic implants, such as prosthetic valves that can be implanted within any of the native valves of the heart (e.g., the aortic, mitral, tricuspid and pulmonary valves). The present disclosure also provides frames for use with such prosthetic implants. The frames can comprise struts having different shapes and/or sizes to avoid coronary blockage and native leaflet overhang. The prosthetic heart valves may also include a plurality of leaflets attached to the frame.

The present disclosure also may include leaflet assemblies for prosthetic heart valves, leaflet commissure tab assemblies of a leaflet assembly, and methods for assembling leaflet commissure tab assemblies. The leaflet commissure tab assemblies may include a plurality of leaflet commissure support members. Each leaflet commissure tab assembly can include a pair of adjacent leaflet tabs coupled to one another by the commissure support member. Each leaflet commissure assembly can be formed by folding and securing a tab of each of the leaflets around a corresponding commissure support member. The adjacently arranged valve leaflets can then be coupled to one another, prior to being attached to the frame of the prosthetic heart valve. As a result, a leaflet assembly for a prosthetic heart valve may be more easily assembled off the frame of the prosthetic heart valve and the time and effort for securing the leaflet assembly to the frame of the prosthetic heart valve may be reduced.

Also disclosed herein are various small diameter prosthetic valves (e.g., 20 mm) that can address one or more of the drawbacks associated with known small diameter prosthetic valves discussed above. In particular, disclosed embodiments can be configured to reduce pressure gradients, avoid native leaflet overhang, and/or maintain access and blood flow to the coronary arteries, all issues commonly associated with smaller diameter valves. Disclosed embodiments can comprise a plurality of commissure tab assemblies of the leaflet assembly being coupled to the outside surface of the frame. The disclosed commissure tab assemblies can, for example, allow the valve leaflets to open wider than generally allowed in conventional valves, which increases the overall blood flow through the prosthetic valve to reduce high-pressure gradients.

Prosthetic valves disclosed herein can be radially compressible and expandable between a radially compressed state and a radially expanded state. Thus, the prosthetic valves can be crimped on or retained by an implant delivery apparatus in the radially compressed state during delivery, and then expanded to the radially expanded state once the prosthetic valve reaches the implantation site. It is understood that the valves disclosed herein may be used with a variety of implant delivery apparatuses.

Figure 1:
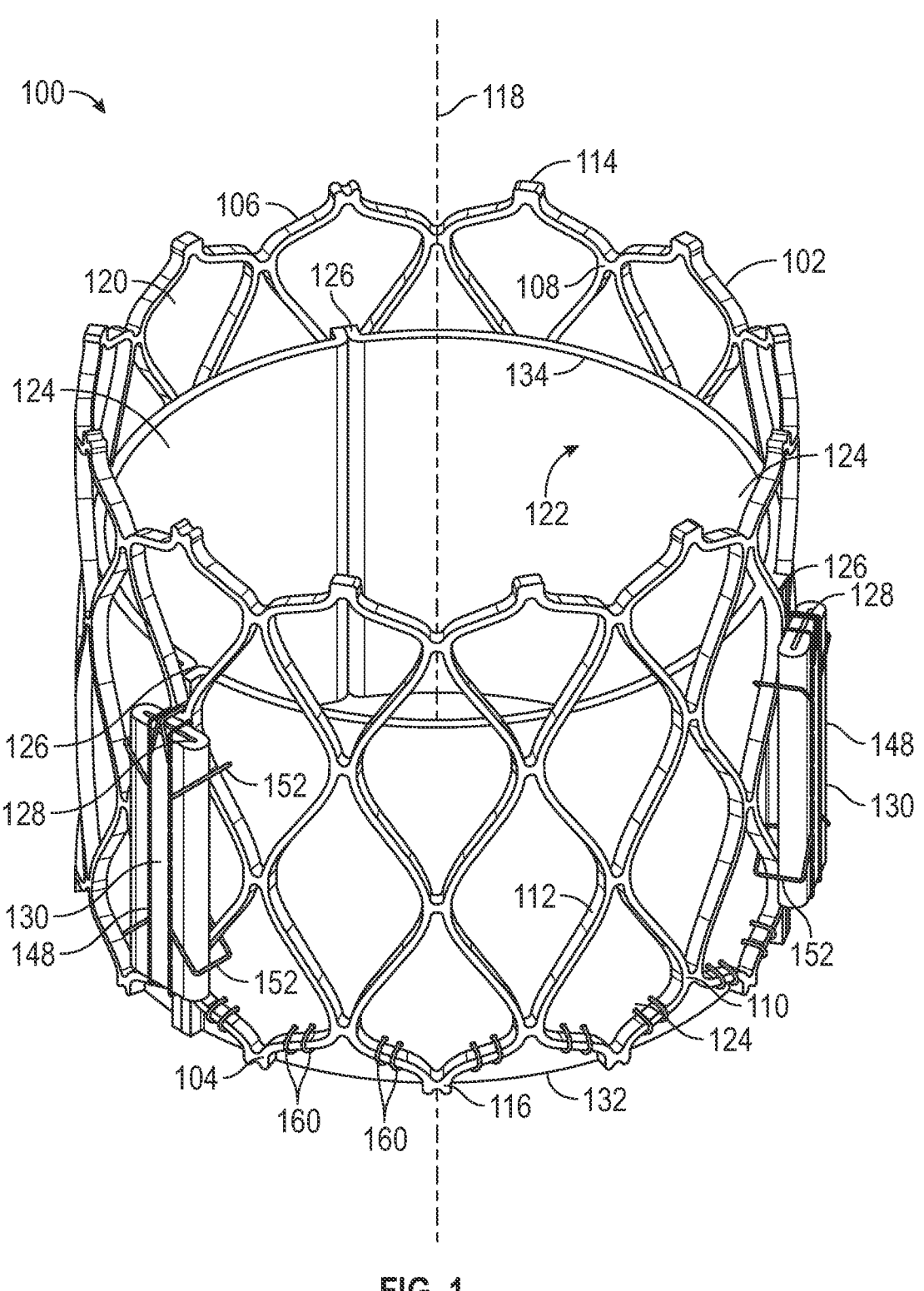
FIG. 1 is a perspective view of a prosthetic heart valve, according to one embodiment.

FIG. 1 shows an exemplary prosthetic heart valve 100, according to one embodiment. The prosthetic heart valve 100 can be radially compressible and expandable between a radially compressed configuration for delivery into a patient and a radially expanded configuration. In particular embodiments, the prosthetic heart valve 100 can be implanted within the native aortic annulus, although it also can be implanted at other locations in the heart, including within the native mitral valve, the native pulmonary valve, and the native tricuspid valve. The prosthetic heart valve 100 can include an annular stent or frame 102 having a first end 104, a second end 106, an inner surface 108, and an outer surface 110.

In the depicted embodiment, the first end 104 is an inflow end and the second end 106 is an outflow end. The outflow end 106 can be coupled to a delivery apparatus for delivering and implanting the prosthetic heart valve within the native aortic valve is a transfemoral, retrograde delivery approach. Thus, in the delivery configuration of the prosthetic heart valve, the outflow end 106 is the proximal-most end of the prosthetic valve. In other embodiments, the inflow end 104 can be coupled to the delivery apparatus, depending on the particular native valve being replaced and the delivery technique that is used (e.g., trans-septal, transapical, etc.). For example, the inflow end 104 can be coupled to the delivery apparatus (and therefore is the proximal-most end of the prosthetic heart valve in the delivery configuration) when delivering the prosthetic heart valve to the native mitral valve via a trans-septal delivery approach.

Figure 2:
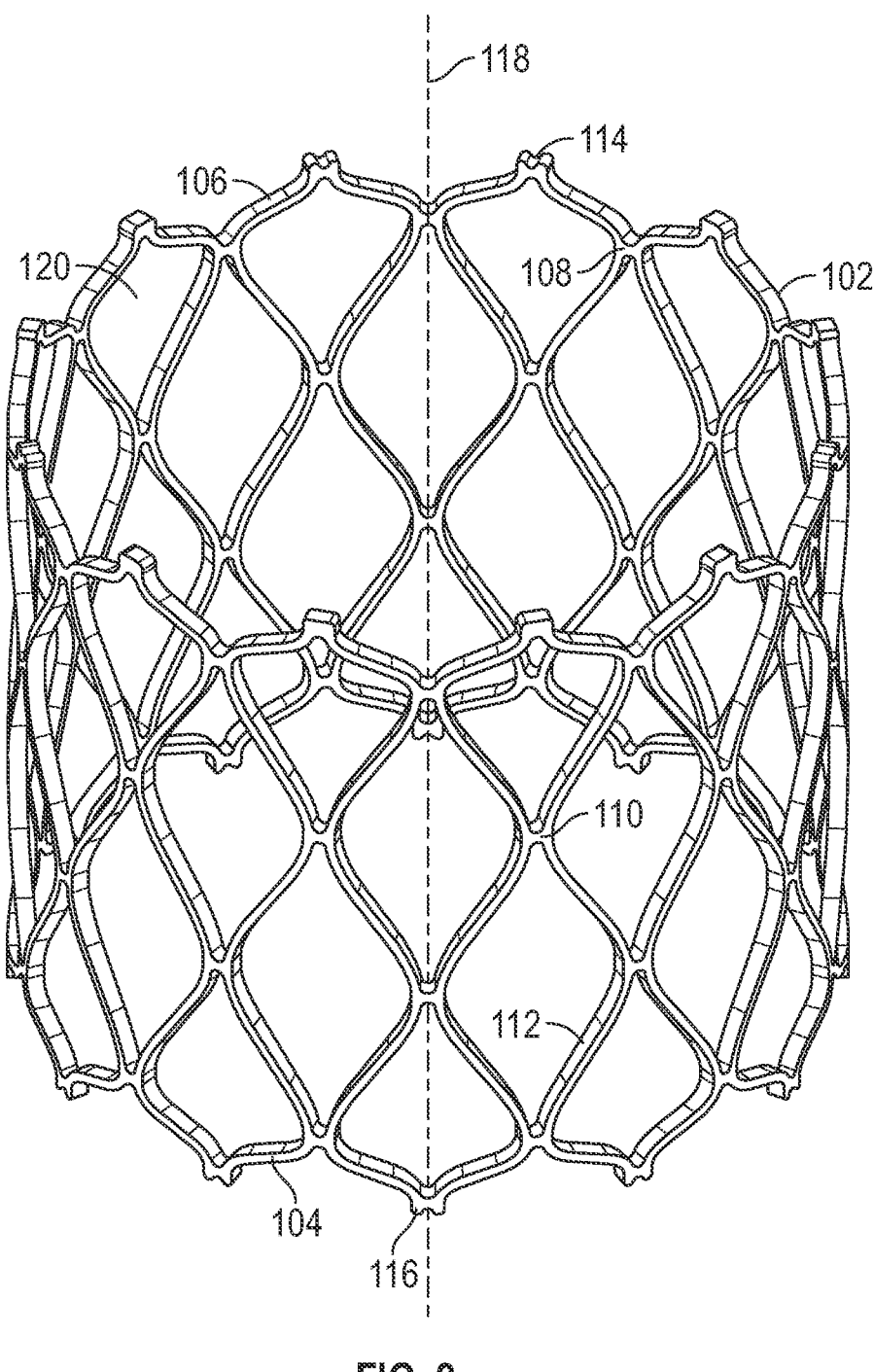
FIG. 2 is a perspective view of the frame of the prosthetic valve of FIG. 1, shown in a radially expanded state.

As shown in FIGS. 1 and 2, the frame 102 can include a plurality of interconnected lattice struts 112 arranged in a lattice-type pattern and forming a plurality of apices 114 at the outflow end 106 of the prosthetic valve 100. The struts 112 can also form similar apices 116 at the inflow end 104 of the prosthetic valve 100. In FIGS. 1 and 2, the struts 112 are shown as positioned diagonally, or offset at an angle relative to, and radially offset from, a longitudinal axis 118 of the prosthetic valve 100 when the prosthetic valve 100 is in the expanded configuration. In other implementations, the struts 112 can be offset by a different amount than depicted in FIG. 1, or some or all of the struts 112 can be positioned parallel to the longitudinal axis 118 of the prosthetic valve 100.

The frame 102 can be made of any of various suitable plastically expandable materials, such as stainless steel or a cobalt chromium alloy, and/or self-expanding materials, such as a nickel titanium alloy ("NiTi"), for example Nitinol. When constructed of a plastically expandable material, the frame 102 (and thus the prosthetic valve 100) can be crimped to a radially compressed state on a delivery catheter and then expanded inside a patient by an inflatable balloon or any suitable expansion mechanism. When constructed of a self-expandable material, the frame 102 (and thus the prosthetic valve 100) can be crimped to a radially compressed state and restrained in the compressed state by insertion into a sheath or equivalent mechanism of a delivery catheter. Once inside the body, the prosthetic valve 100 can be advanced from the delivery sheath, which allows the valve to expand to its functional size.

Referring still to FIGS. 1 and 2, the frame 102 can include a plurality of circumferentially extending rows of interconnected struts 112 arranged in a lattice-type pattern. In the illustrated embodiment, the open lattice structure of the frame 102 can define rows of a plurality of open frame openings 120 between the struts 112. As shown in FIGS. 1 and 2, the frame openings 120 can be diamond shaped. The frame openings 120 are arranged in a plurality of circumferentially extending rows, including a lowermost row at the inflow end of the frame, an uppermost row at the outflow end of the frame, and one or more intermediate rows between the lowermost row and uppermost row. In the illustrated embodiment, there are four rows of frame openings, and all of the openings within a given row are of the same size and shape.

In the illustrated embodiment, the struts 112 are pivotable or bendable relative to each other to permit radial expansion and contraction of the frame 102. For example, the frame 102 can be formed (e.g., via laser cutting, electroforming or physical vapor deposition) from a single piece of material (e.g., a metal tube). As such, the inflow end 104 and the outflow end 106 of the frame 102 can move axially parallel to the longitudinal axis 118 of the prosthetic valve 100 as it is radially expanded or compressed, such as during assembly, preparation, or implantation of the prosthetic valve 100.

In other embodiments, the frame 102 can be constructed by forming individual components (e.g., the struts and fasteners of the frame) and then mechanically assembling and connecting the individual components together. For example, the struts 112 can be pivotably coupled to one another at one or more pivot joints or pivot junctions along the length of each strut. Each of the pivot joints or pivot junctions (e.g., hinges) can allow the struts 112 to pivot relative to one another as the frame 102 is radially expanded or compressed.

Further details regarding the construction of the frame and the prosthetic valve are described in U.S. Patent Publication Nos. 2018/0028310, which is incorporated herein by reference. Other frames that can be implemented in the prosthetic valve are disclosed in U.S. Publication Nos. 2012/0123529, 2012/0239142 and 2018/0153689, which are incorporated herein reference.

The prosthetic valve 100 can also include a valvular structure 122 which is coupled to and supported by the frame 102. The valvular structure 122 is configured to regulate the flow of blood through the prosthetic valve 100 from the inflow end 104 to the outflow end 106. The valvular structure 122 can include, for example, a leaflet assembly comprising one or more leaflets 124 made of a flexible material. The leaflets 124 can be made in whole or in part, from biological material, bio-compatible synthetic materials, or other such materials. Suitable biological material can include, for example, bovine pericardium (or pericardium from other sources). The leaflets 124 can be secured to one another at their adjacent sides to form commissures 126, each which can be secured to a commissure support member 128, as discussed further below.

As shown FIGS. 3-5A, each leaflet 124 of the valvular structure 122 can be configured to have a quadrilateral shape (e.g., rectangular as shown or square) and can have an inflow edge 132 and an outflow edge 134 (also referred to as a coaptation edge) that contacts respective outflow edges of the other leaflets during closure of the leaflets 124 (e.g., during diastole).

Leaflets commonly found in prosthetic valves typically have a curved, scallop shape, such as a lower cusp edge portion curving between the tabs of each of the leaflets. As a result, the prosthetic leaflets are often attached to the frame in a scalloped pattern with their lowest most point (e.g., the closest most point to the inflow end of the valve), offset from the inflow end of the valve.

Figure 3:
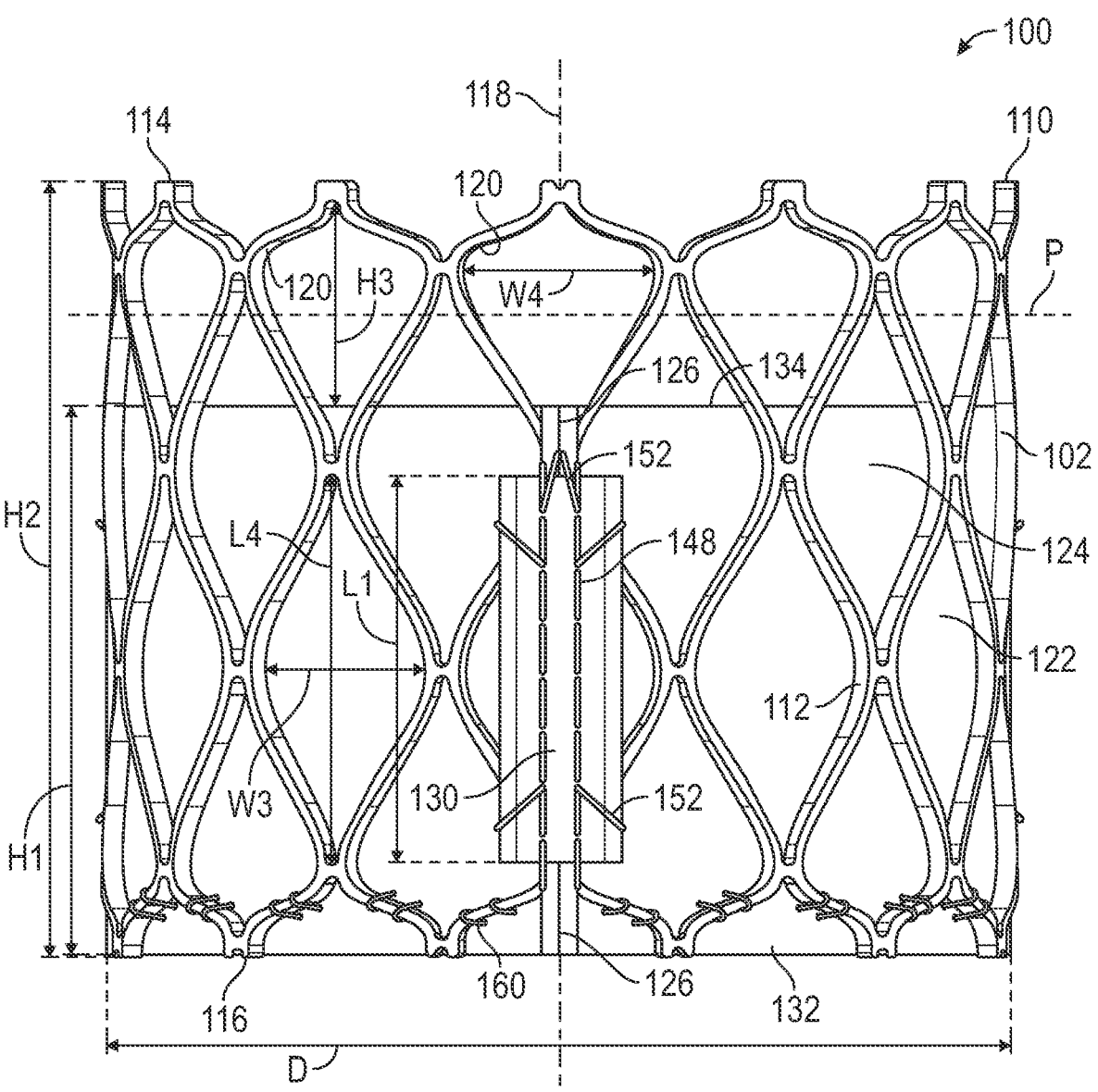
FIG. 3 is a side elevation view of the prosthetic heart valve of FIG. 1.
Figure 4:
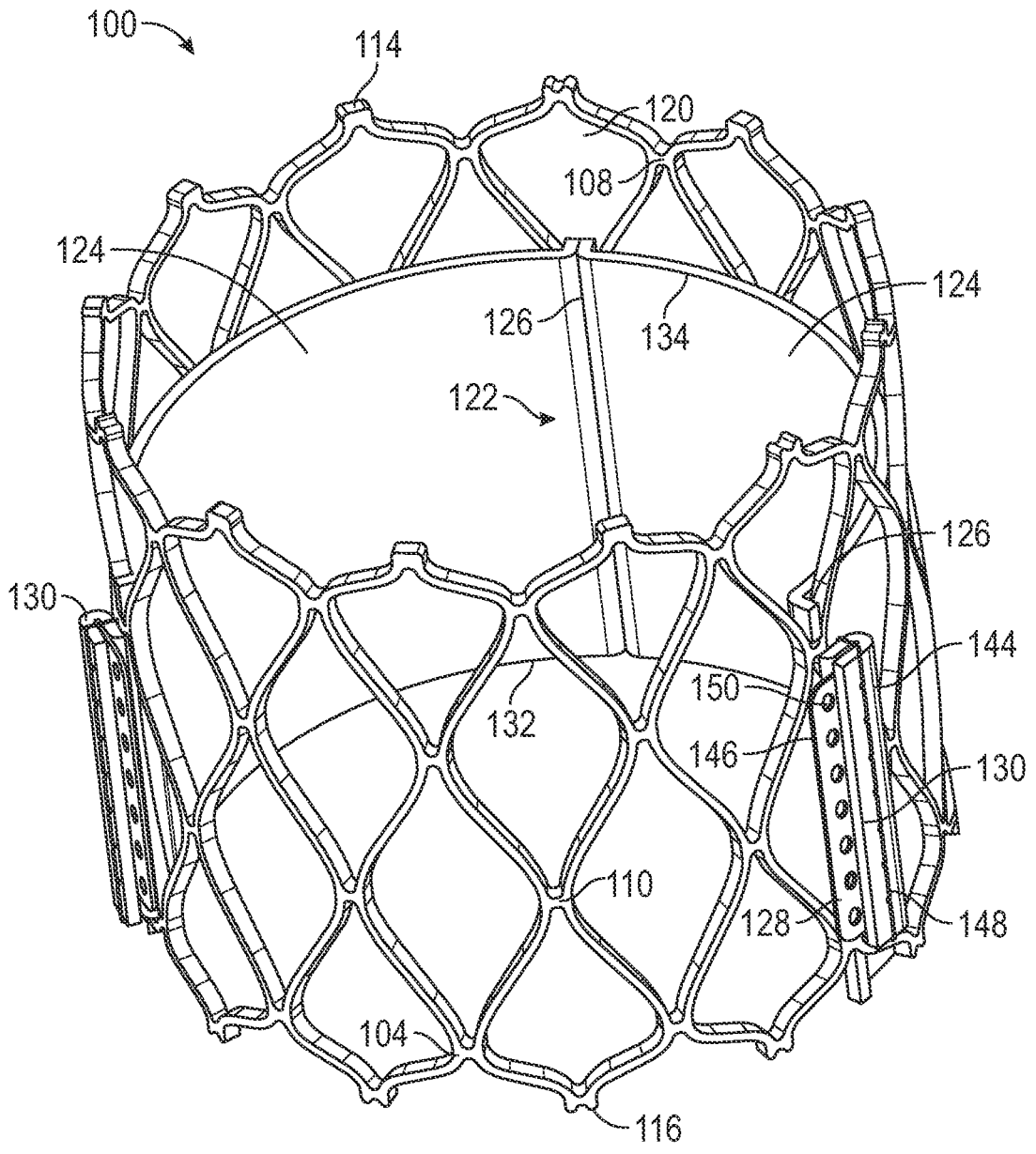
FIG. 4 is a perspective view of the prosthetic heart valve of FIG. 1, shown with one of the leaflets removed for purposes of illustration.

As shown in FIGS. 1 and 3-4, the inflow edges 132 of the quadrilateral shaped leaflets 124 of the valvular structure 122 can be aligned with (or substantially aligned with) and attached to the inflow end 104 of the frame 102. As such, each of the leaflets 124 can also have an outflow end 134 which is offset axially from the outflow end 106 of the frame along the longitudinal axis 118 of the valve 100. In this manner, the outflow edge 134 of each leaflet can be located between the inflow end 104 and the outflow end 106 of the frame 102, leaving the frame openings 120 or portions thereof that are downstream of the outflow edge open and accessible during the working cycle of the prosthetic valve 100, thereby reducing potential blockage of the coronary arteries by the leaflets 124.

As best shown in FIG. 3, the outflow edges 134 of the leaflets 124 are upstream of a plane P that is perpendicular to the longitudinal axis 118 and bisects each of the openings 120 of the uppermost row of openings at the outflow end of the frame. In this manner, a majority of each of the frame openings 120 in the uppermost row are uncovered by the leaflets 124 in their open position, thereby providing access to the coronary arteries. In some embodiments, at least 60% of the frame openings in the uppermost row are uncovered by the leaflets 124 in their open position; and more desirably, at least 80% of the frame openings in the uppermost row are uncovered by the leaflets 124 in their open position; and more desirably at least 80% of the frame openings in the uppermost row are uncovered by the leaflets 124 in their open position; and more desirably at least 90% of the frame openings in the uppermost row are uncovered by the leaflets 124 in their open position; and more desirably 100% of the frame openings in the uppermost row are uncovered by the leaflets 124 in their open position.

Figures 5A, 5B:
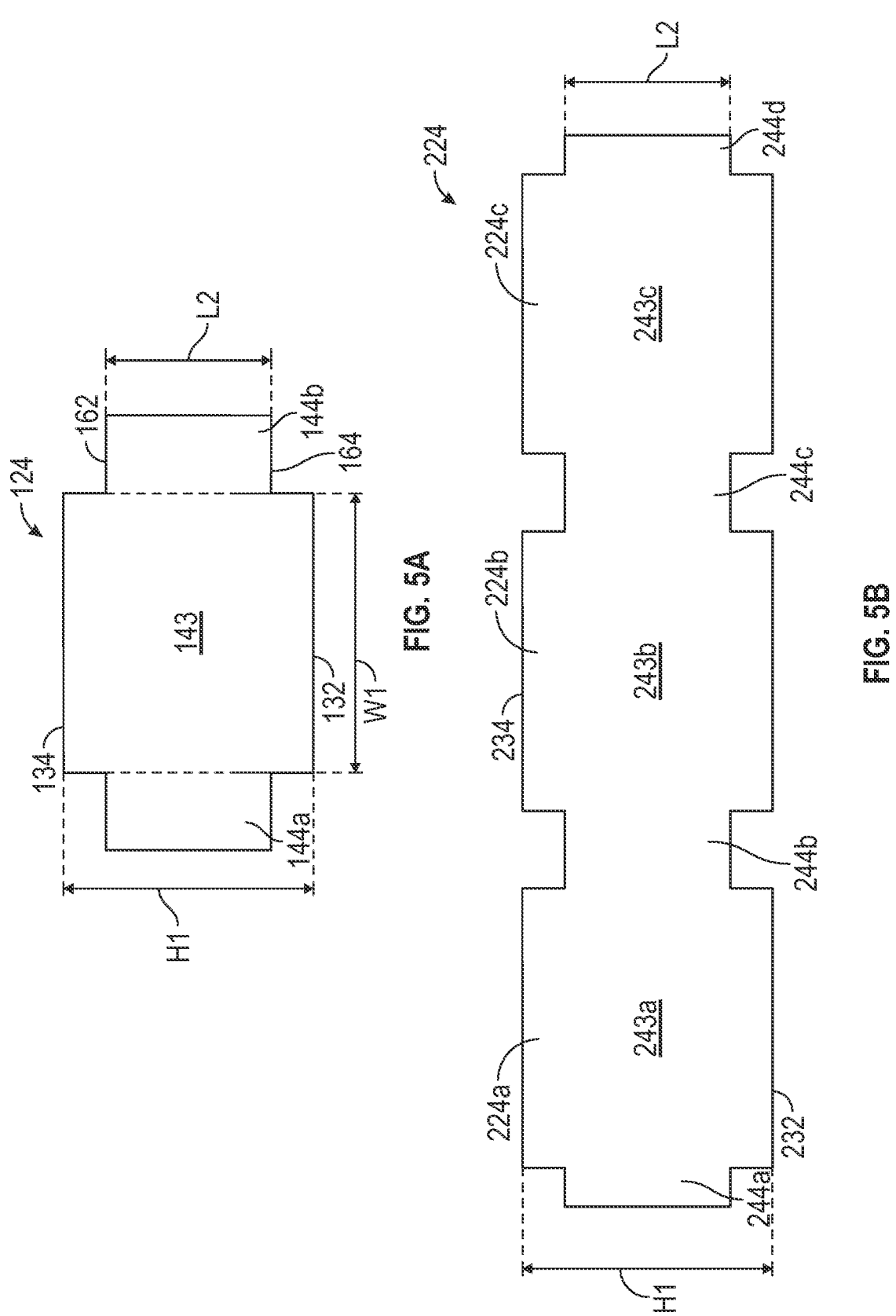
FIGS. 5A-5D are plan views of four different leaflet embodiments that can be used in the prosthetic valve of FIG. 1.

As shown in FIG. 5A, each leaflet 124 of the valvular structure 122 can have a main body 143 defining an inflow edge 132 and an outflow edge 134 and leaflet tabs 144a, 144b (also referred to as commissure tabs) extending from opposite sides of the main body 143. Each leaflet 124 can have a leaflet height H1 which is defined by the length extending from the inflow edge 132 (e.g., at the inflow end 104) to the outflow edge 134 and width W1 measured from one side of the main body 143 to the other side of the main body. In the illustrated embodiment, each leaflet 124 is rectangular in shape having a width W1 greater than a height H1. Although the prosthetic valve 100 is described herein with quadrilateral leaflets, other configurations and constructions are leaflets may be used.

As further shown in FIG. 5A, each leaflet tab 144a, 144b in the illustrated embodiment has a height or length L2 measured from an outflow edge 162 of the leaflet tab to an inflow edge 164 of the leaflet tab 164. The outflow edge 162 can be axially offset from the outflow edge 134 of the main body 143 in an upstream direction and the inflow edge 164 can be axially offset from the inflow edge 132 of the main body 143 in a downstream direction.

The frame 102 can also have a diameter D and a height H2 which is defined by the length of the frame 102 that extends along the longitudinal axis 118 between the most outward point of the apices 116 of the inflow end 104 and the apices 114 of the outflow end 106.

Selection of the height of the frame of a prosthetic valve is an important consideration, especially for smaller diameter prosthetic valves (e.g., 20 mm or smaller). Generally speaking, the frame of a prosthetic valve desirably should be short enough to avoid extending beyond the sinotubular junction (STJ) line and tilting of the prosthetic valve from its intended implanted orientation, yet long enough to avoid native leaflet overhang. It has been found by the present inventors that for patients needing a relatively smaller prosthetic valve (20 mm or smaller), a prosthetic valve having a height of about 14 mm or shorter can increase the risk of leaflet overhang while a prosthetic valve having a height of over 18 mm is likely to extend beyond the STJ line.

Selection of the height of the individual leaflets is also an important consideration for smaller diameter prosthetic valves. Generally speaking, the leaflets should be high enough to promote full closure of the leaflets during diastole, for example, to prevent unwanted back flow through the prosthetic valve. On the other hand, the leaflets should also be low enough as to not block access to the coronary arteries when in an opened and closed configuration.

Therefore, in some embodiments, the prosthetic valve 100 can have a valve diameter D in the range of 18 mm to 22 mm, and more particularly 19 mm to 21 mm, with 20 mm being a specific example; the frame height H2 can be in the range of 15 mm to 18 mm, and more particularly 16 mm to 17 mm, with 15.5 mm being a specific example; and each leaflet 124 can have a height H1 in the range of 11 mm to 14 mm, and more particularly 12 mm to 13 mm, with 12 mm being a specific example. It has been found by the present inventors that a prosthetic valve having these dimensions can decrease the risk of leaflet overhang while avoiding the STJ line, and can also achieve full closure of the leaflets while avoiding blocking coronary access.

In addition, the use of quadrilateral leaflets 124 allows the prosthetic valve 100 to be constructed with a minimal leaflet height H1 (e.g., 11 mm). For example, the quadrilateral shape of the leaflets 124 increases the surface area of the leaflets 124 in contact with the blood flood entering the valve 100 without having to use higher (e.g., longer) leaflets, which is generally utilized in valves having scallop shaped leaflets. By constructing the prosthetic valve 100 with quadrilateral leaflets 124, having a low leaflet height H1, the resistance across the valve 100 can be reduced and the opening of the leaflets widens during working cycles of the valve. As such, the total pressure gradient across the valve can be reduced. In some embodiments, the pressure gradient across the prosthetic valve 100 can be further reduced by utilizing smooth leaflets and/or thinning the leaflets by, for example, sourcing, skiving, and/or laser milling.

According to embodiments described herein, the diameter D and height H2 of the frame 102 can have a proportional relationship with respect to each other and each can have a proportional relationship with respect to the leaflet height H1 of the leaflets 124. For example, the prosthetic valve 100 can have a ratio D/H2 in the range of about 1.24 to 1.34, a ratio D/H1 in the range of about 1.61 to 1.71, and a ratio H2/H1 in the range of about 1.24 to 1.34. In some embodiments, the prosthetic valve 100 can have a ratio D/H2 in the range of about 1.0 to 1.5, a ratio D/H1 in the range of about 1.3 to 1.9, and a ratio H2/H1 in the range of about 1.0 to 1.5, as the dimensions of the prosthetic valve are adjusted. In other embodiments, the ratio D/H2 is about equal (or substantially equal) to the ratio H2/H1. In further embodiments, the ratio D/H1 is greater than or equal to the ratio D/H2 and/or the ratio H2/H1.

Referring to FIG. 3, in some embodiments, one or more of the frame openings 120 above the outflow edge 134 of the leaflets 124 has a maximum width W4 and a height H3 (measured from the outflow edge of a leaflet to the inner edge of an apex 114) greater than the diameter of a native ostia. In particular embodiments, the width W4 and the height H3 is at least 2 millimeters (which can allow passage of a 6 Fr coronary catheter through the openings), or at least 4 millimeters in some embodiments, or at least 6 millimeters in some embodiments. In some embodiments, one or more of the frame openings 120 above the outflow edge 134 has a width W4 and a height H3 double the diameter of a native ostia in which the prosthetic valve is implanted.

In the illustrated embodiment, the frame 102 has twelve openings 120 within each row of openings. In other embodiments, each row of openings 120, or at least the row at the outflow end of the frame can have a smaller number of openings 120 to increase the maximum width W4 of each opening. For example, in some embodiments, at least the upper row at the outflow end of the frame can have nine openings 120. Moreover, the number of rows of openings along the height H2 of the frame 102 can be less than four, such as two or three rows of openings 120, to increase the height H3 of at least the row of openings at the outflow end of the frame.

FIG. 4 shows a perspective angle of the prosthetic valve 100 with one of the leaflets 124 of the valvular structure 122 removed for purposes of illustration. As shown in FIG. 4, the valvular structure 122 can comprise a leaflet assembly having a plurality of the leaflets 124, leaflet contact regions 126, and commissure tab assemblies 130.

As shown in FIG. 5A, each leaflet 124 of the prosthetic valve 100 (e.g., FIG. 1) can have a pair of opposing leaflet tabs 144a, 144b (e.g., opposing side portions) extending laterally from a main body 143 of the leaflet between the inflow edge 132 and the outflow edge 134 of the main body 143 wherein the edges 132, 134 define the height H1 of the leaflet 124 and the main body 143. In the illustrated embodiment, the leaflet tabs 144a, 144b can have a length L2 having a dimension that is less than the height H1 of the leaflet. In this configuration, the leaflet tabs 144a, 144b can extend circumferentially around a respective support member 128 and are able to extend through an opening 120 without deforming the main body 143 of the leaflet 124 positioned within the interior of the frame 102. As such, the leaflet tabs 144a, 144b can have a length L2 equal to (or substantially equal to) the length L1 of the commissure tab assemblies 130.

Figure 6:
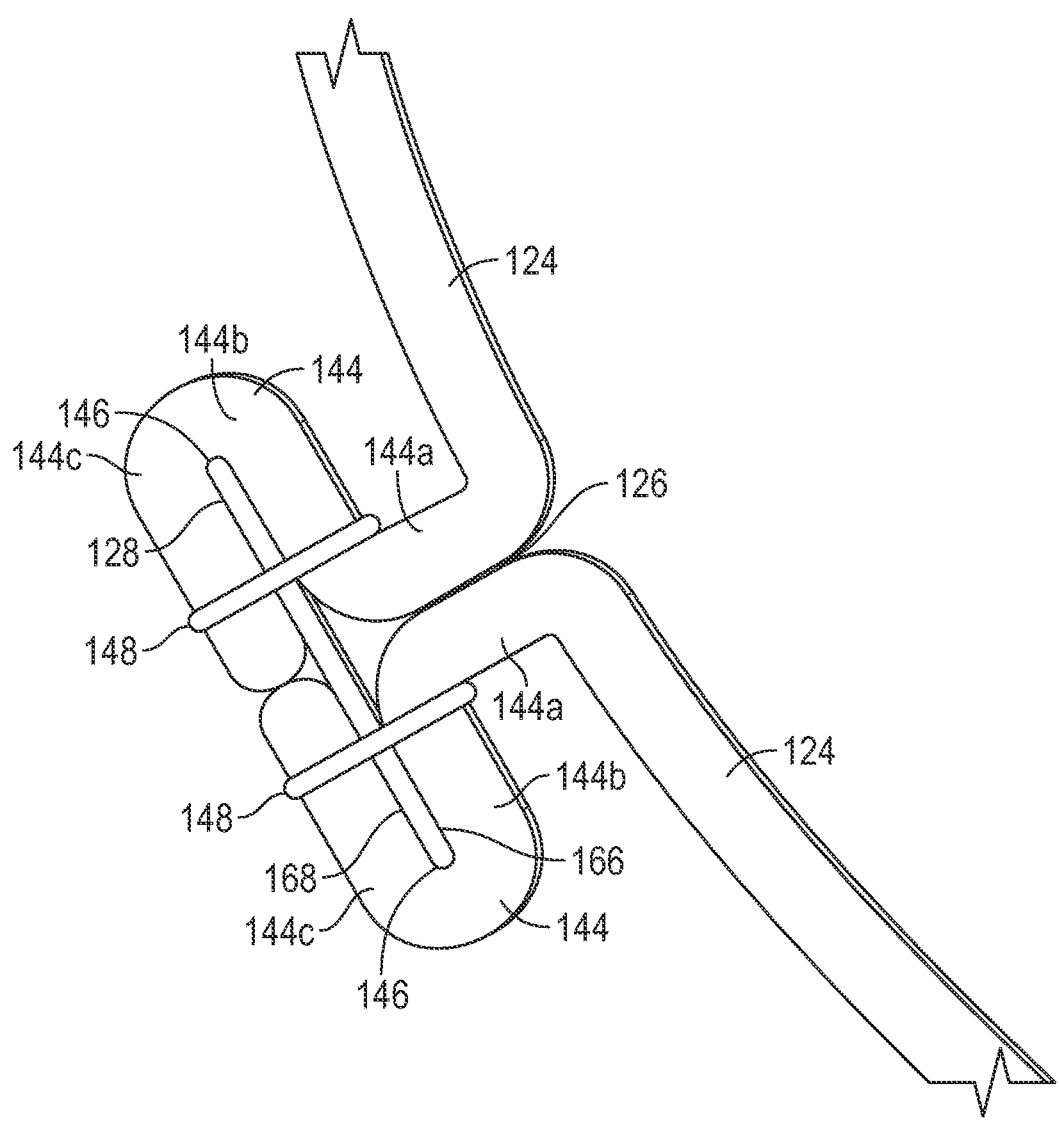
FIG. 6 is a plan view of a commissure tab assembly for the prosthetic heart valve of FIG. 1.

Referring to FIGS. 4 and 6, each commis sure tab assembly 130 of the valvular structure 122 can include a pair of leaflet tabs 144 connected to a respective support member 128. For example, as shown in FIG. 6, each pair of leaflet tabs 144 from adjacent leaflets 124 (e.g., individual leaflets 124) can be in contact with one another to form a respective contact region 126 from which each of the leaflet tabs 144 extends and wraps around the surface (e.g., inner and outer surfaces) of a respective commissure support member 128.

As shown in FIG. 6, each leaflet tab 144 can form a first, radially extending fold 144a, a second, circumferentially extending fold 144b radially inside of the support member 128, and a third, circumferentially extended fold 144c radially outside of the support member 128. The second fold 144b extends along an inner surface 166 of the support member 128 and third fold extends along an outer surface 168 of the support member 128. In some embodiments, each of the leaflet tabs 144 can extend and wrap around the commissure support members 128 such that one leaflet tab overlaps the other.

In the illustrated embodiment, each support member 128 is in the form of a rectangular plate having flat and parallel inner and outer surfaces 166, 168. In alternative embodiments, the support members 128 can have various other shapes, such as cylindrical, square, etc.

The leaflet tabs 144 can be also be secured to the commissure support member 128 by one or more sutures 148 extending through and/or around each of the adjacent leaflet tabs 144 and commissure support member 128 to form a commissure tab assembly 130. For example, as best shown in FIG. 4, each leaflet tab 144 can be secured to a commissure support member 128 with one or more sutures 148 forming in-and-out stitches extending through the second fold 144b, apertures 150 in the commissure support member 128, and the third fold 144c.

As shown in FIGS. 4 and 7A-7C, the commissure support member 128 can be a rigid plate-like structure (or partially rigid structure) made of various materials, including a polymer, stainless steel, a cobalt chromium alloy, or Nitinol, and/or a combination thereof and have a plurality of apertures 150 sized and arranged to receive one or more sutures 148. In the illustrated embodiments of FIGS. 4 and 7A, the apertures 150 of the support member 128 are arranged in two columns (or alternatively rows) along the length L3 and side portions 146 of the commissure support member 128. The arrangement of apertures 150 shown in FIG. 7A can, for example, allow for one or more sutures 148 to extend in and out of the apertures 150 and through the second and the third folds 144b, 144c of the leaflet tabs 144, such as in the illustrated embodiment depicted in FIG. 4. In some embodiments, the length L3 of the support member 128 can be greater than, less than, or equal to the height H1 of the leaflets 124 and/or the length L2 of the leaflet tabs 144.

Figures 7A, 7B:
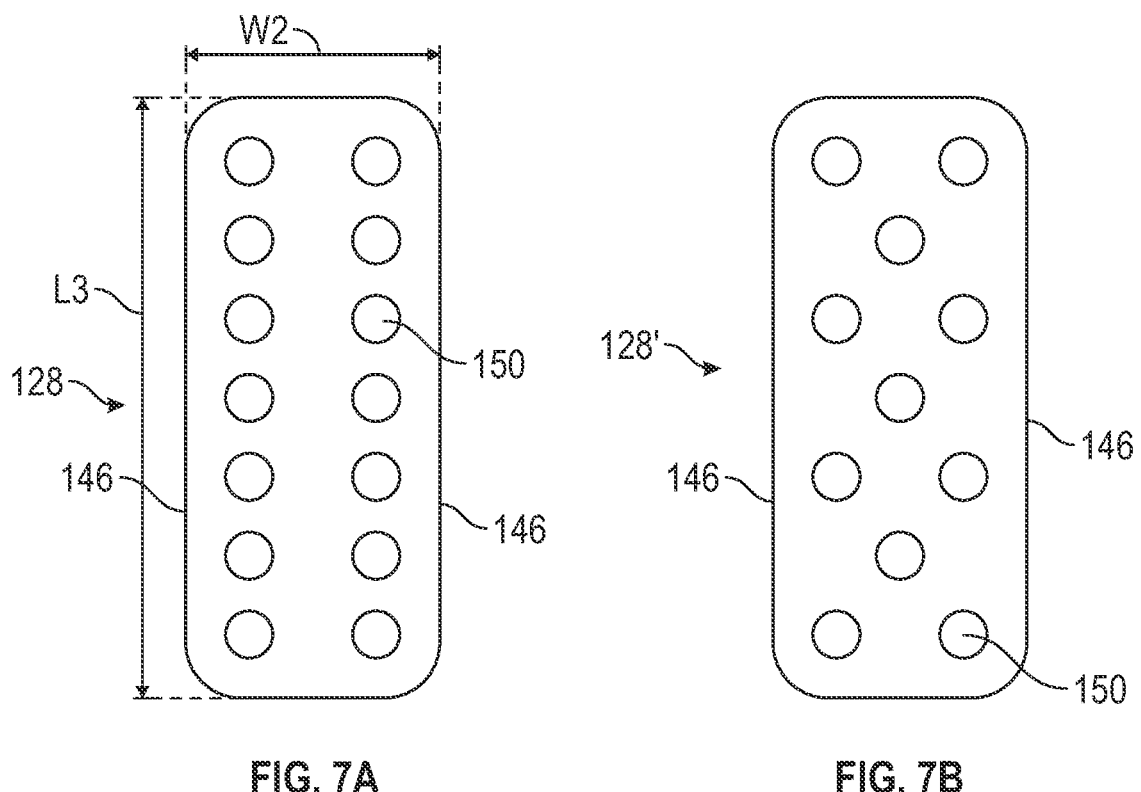
FIGS. 7A-7C are front views of different embodiments of a commissure support member that can be used in forming the commissure tab assemblies of the prosthetic valve of FIG. 1.
Figure 7C:
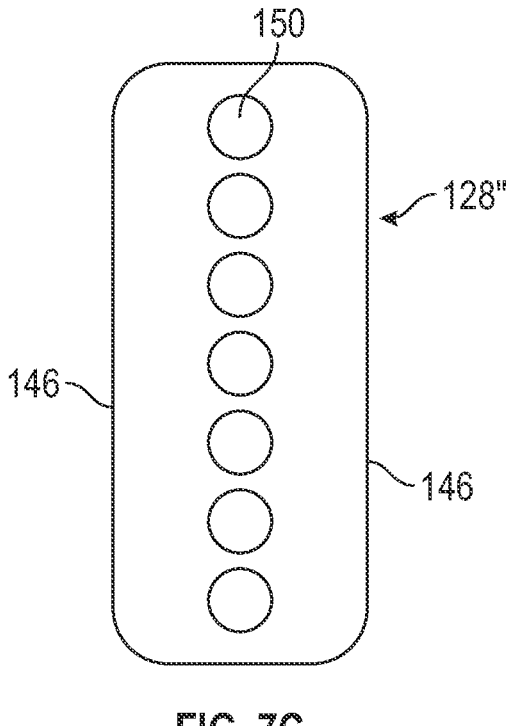

In other embodiments, such as the illustrated embodiments shown in FIGS. 7B-7C, the apertures 150 of a support member can be arranged in various configurations. For example, as shown in FIG. 7B, a support member 128' can have an alternating (or staggering) configuration such that one of the two rows repeated along the length of the support member can have one or more additional apertures 150 than the other. Alternatively, as shown in FIG. 7C, a support member 128" can have a single column of apertures 150 arranged in a straight line along the length (e.g., L3) of the commissure support member 128". In some embodiments, the support members can have any number, arrangement, diameters, and/or shape of apertures 150 to receive one or more sutures 148.

Figure 8:
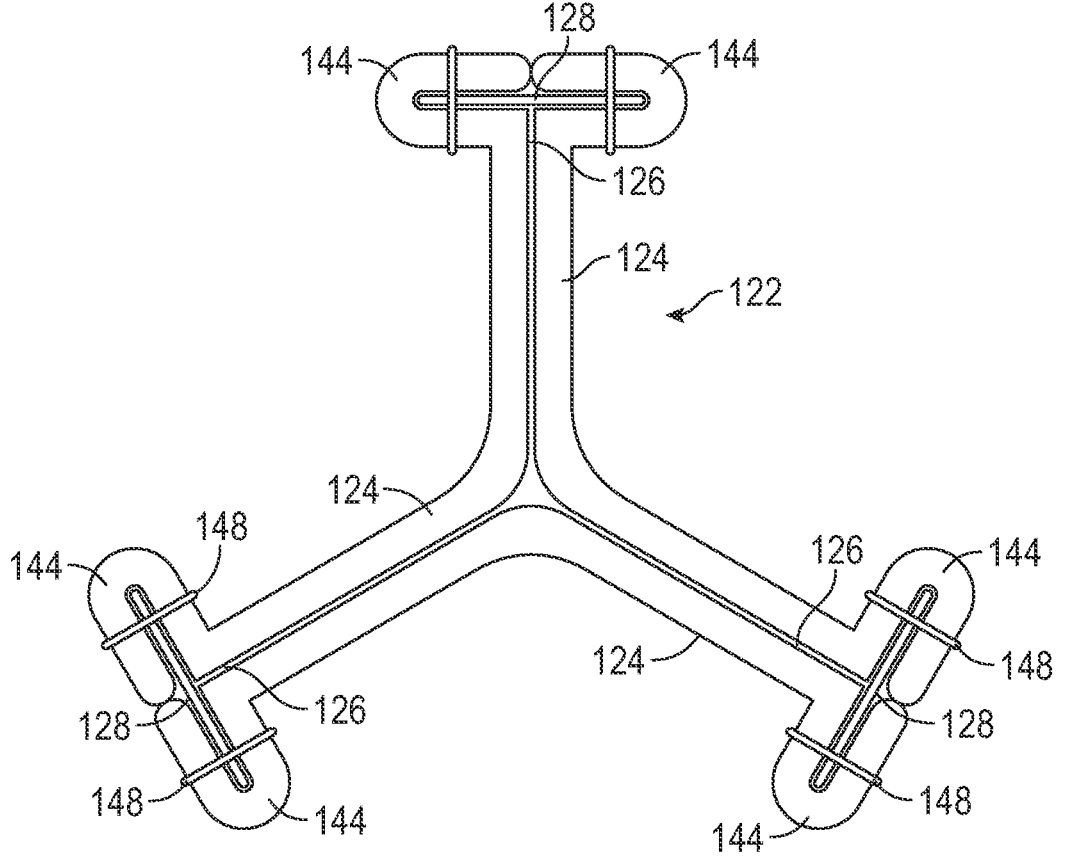
FIG. 8 is a top plan view of a preassembled valvular structure for insertion into the prosthetic valve frame, such as the frame of FIG. 2.
Figure 9:
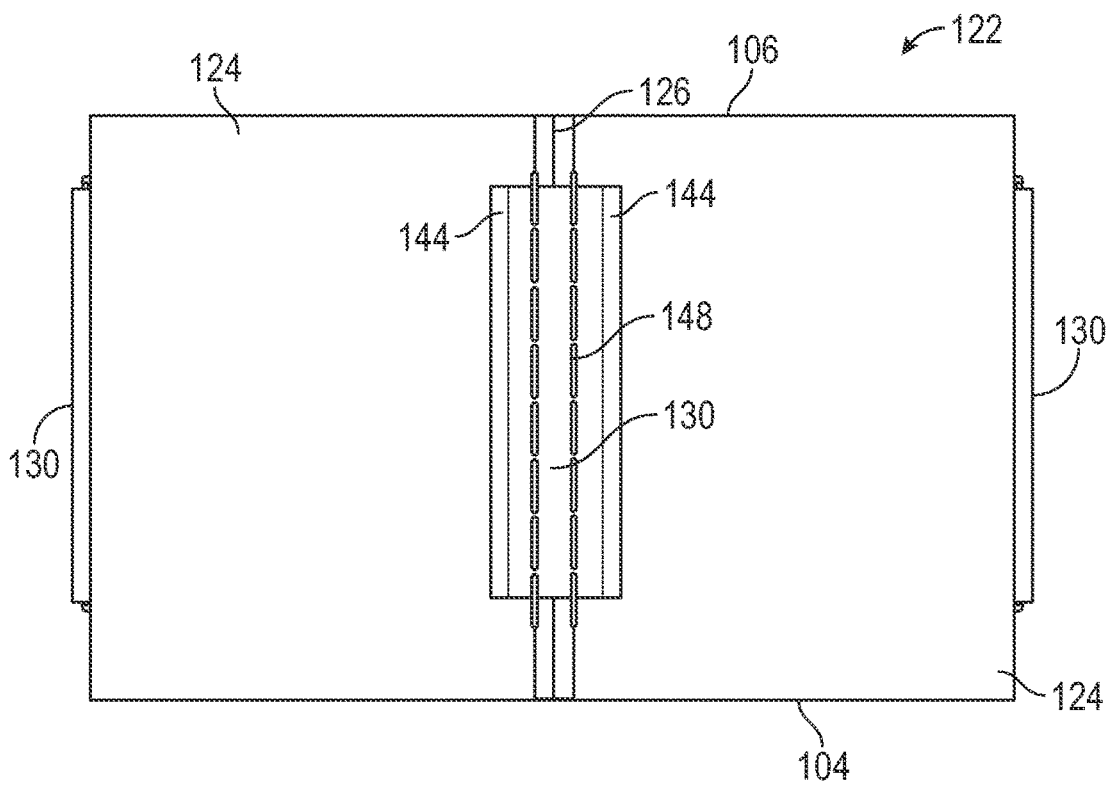
FIG. 9 is a side view of the preassembled valvular structure of FIG. 8.

In a typical prior art valve construction, a leaflet assembly comprising multiple leaflets connected at adjacent tabs is placed within a frame and the commissure assemblies are formed by stitching the leaflets tabs to support members of the frame and/or to other soft components, such as fabric reinforcing members. As can be appreciated, the process of forming the commissure assemblies and securing them to the frame is a time-consuming and pain staking process. According to the commissure tab assemblies 130 described herein, the valvular structure 122 of the prosthetic valve 100 can be preassembled prior to its insertion into and attachment to the frame 102. For example, FIGS. 8 and 9 depict a preassembled valvular structure 122 with the leaflet tabs 144 of each leaflet 124 wrapped around and secured (e.g., by sutures 148) to respective commissure support members 128. In this manner, the entire valvular structure, including the commissure tab assemblies 130, can be preassembled prior to placing the leaflets within the frame, which can significantly reduce the overall assembly time of the prosthetic valve.

The preassembled valvular structure 122 of FIGS. 8 and 9 can, for example, be positioned within (or partially within) an interior (e.g., proximate to the inner surface 108) of the frame 102 (e.g., the bare frame of FIG. 2) such that each of the commissure tab assemblies 130 can be inserted into and through a respective open frame opening 120 to position the commissure tab assemblies 130 on an exterior (e.g., the outer surface 110) of the frame 102. The commissure assemblies 130 can be deformed at folds 144a to facilitate insertion of the commissure assemblies through respective openings 120.

For example, once the valvular structure 122 is positioned within the frame 102, the commissure tab assemblies 130 can be twisted (e.g., turned, rotated, pivoted, etc.) at folds 144a relative to the main bodies 143 of the leaflets and the frame 102 (e.g., 90 degrees). This allows one end of each of the commissure tab assemblies 130 to be inserted through a respective open frame opening 120 until the entirety of each commis sure tab assembly 130 is advanced through the frame opening 120. Once each of the commissure tab assemblies 130 reach the exterior of the frame 102, the commis sure tab assemblies 130 can be twisted or moved back to their non-deformed shape so that they extend parallel to the longitudinal axis 118 along the outer surface of the frame 102. As such, each of the commissure tab assemblies 130 can be disposed on the outer surface 110 of the frame 102, the folds 144a extend through openings 120, and the main body of the leaflets are disposed inside of the frame 102.

Each of the support members 128 can have a dimension that is greater than a dimension of the frame opening 120 through which it was inserted to prevent the commissure assembly 130 from being pulled back inwardly into the interior of the frame under normal working pressures. For example, in the illustrated embodiment, the commissure support members 128 can have a length L3 (FIG. 7A) greater than a height L4 (FIG. 3) of the respective open frame openings 120 through which the commissure tab assemblies extend to prevent the commis sure tab assemblies 130 from being pulled back through the open frame openings 120 under normal working pressures once on the exterior of the frame 102. In lieu of or in addition to have a length L3 greater than a height L4 of opening 120, each support member 128 can have a width W2 (FIG. 7A) greater than a width W3 (FIG. 3) of a respective opening to resist pull through of the commis sure assembly 130.

Once disposed on the outer surface 110, the commissure tab assemblies 130 can be connected (e.g., sutured) to the frame 102 with the one or more sutures 152 that can, for example, extend through the leaflet tabs 144 (e.g., through folds 144a, 144c), one or more selected apertures 150 of the commissure support member 128, and around (or through) the struts 112 of the frame 102.

Figures 5C, 5D:
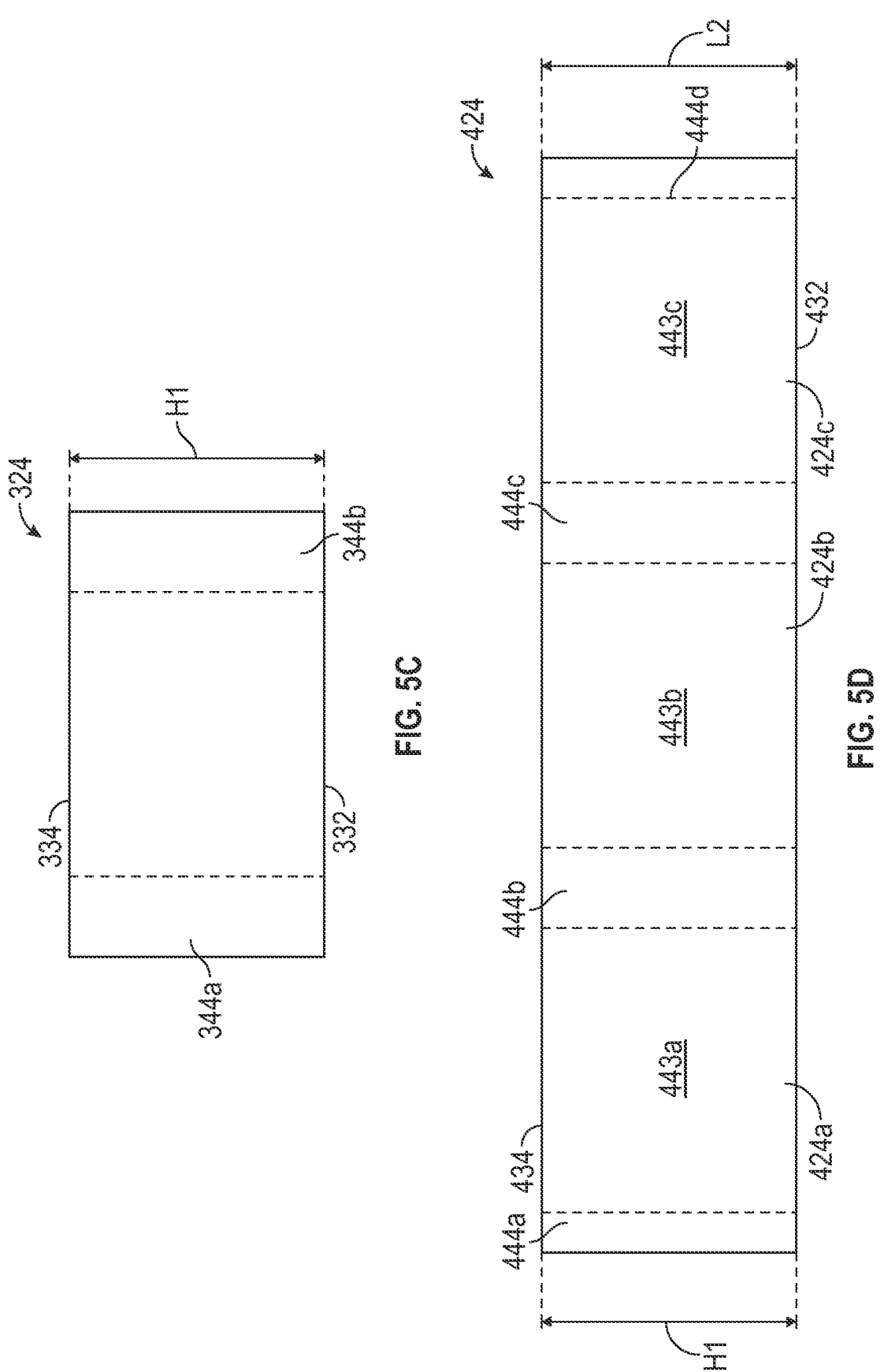

The valvular structure 122 can also be constructed using any of various leaflet configurations, such as those leaflets shown in the embodiments of FIGS. 5B-5D. As shown in FIG. 5B, a valvular structure 224 can be constructed from a single, unitary piece of leaflet material (e.g., a single piece of pericardium) as opposed to individual pieces (e.g., leaflets 124). For example, in the illustrated embodiment of FIG. 5B, the valvular structure 224 can define a plurality of leaflets 224a, 224b, 224c, each having a main body 243a, 243b, 243c, respectively. Each main body has inflow and outflow edges 232, 234. The main bodies can be interconnected to each other with integral intermediate leaflet tabs 244b and 244c. The main body 243a can have an integral outermost tab 244a on one side of the valvular structure and the main body 243c can have an integral outermost tab 244d on the other side of the valvular structure.

The valvular structure 224 can be assembled with a plurality of support members 128 similar to that shown in FIG. 8 by wrapping each intermediate tab 244b, 244c around a respective support member 128 and suturing the tabs to the support member as previously described for the valvular structure 122 to form respective commissure assemblies 130. The two outermost tabs 244a, 244d can be wrapped around and sutured to the same support member 128 to form another commissure assembly 130. The pre-assembled val-vular structure 224 can then be placed into and secured to the frame 102 as previously described for the valvular structure 122.

The leaflets 224a, 224b, 224c cam have the same (or substantially the same) dimensions as described above for the leaflets 124, such as the height H1 of the leaflet and/or the length L2 of the leaflet tabs.

As shown in FIGS. 5C-5D, a valvular structure can be constructed with individual or unitary leaflets having differ-ent leaflet tab dimensions. For example, FIG. 5C shows an individual leaflet 324 having opposing leaflet tabs 344a, 344b extending the height H1 (e.g., L2 is equal to H1) as defined by the inflow and outflow edges 332, 334. In this manner, the leaflet tabs 344a, 344b can provide additional strength, support, and/or be configured for larger openings 120 within the frame 102.

FIG. 5D shows a valvular structure 424 that can be constructed from a single, unitary piece of leaflet material (e.g., a single piece of pericardium) as opposed to individual pieces (e.g., leaflets 324). The valvular structure 424 can define a plurality of leaflets 424a, 424b, 424c, each having a main body 443a, 443b, 443c, respectively. Each main body has inflow and outflow edges 432, 434. The main bodies can be interconnected to each other with integral intermediate leaflet tabs 444b and 444c. The main body 443a can have an integral outermost tab 444a on one side of the valvular structure and the main body 443c can have an integral outermost tab 444d on the other side of the valvular struc-ture. The valvular structure 424 can be assembled with support members 128 in the same manner as described above for the valvular structure 224. In this example, the overall height H1 of the leaflets can be equal to the length L2 of the leaflet tabs.

As shown in FIG. 1, the inflow edge 132 of each leaflet 124 can be connected to the frame 102, such as with one or more sutures 160 extending through the leaflet and around (or through) the struts 112 that form a ring at the inflow end 132 of the frame 102. In some embodiments, the inflow ends of the leaflets can be reinforced at their connection to the frame with one or more reinforcing strips (e.g., fabric strips) extending circumferentially along an outer surface and/or an inner surface of each leaflet. Further details regarding the attachment of the inflow edges of leaflets with and without reinforcing strips are disclosed in U.S. Pat. No. 7,510,575 and U.S. Patent Publication Nos. 2018/0028310, 2012/0123529, and 2012/0239142, which are incorporated herein by reference.

Figure 10:
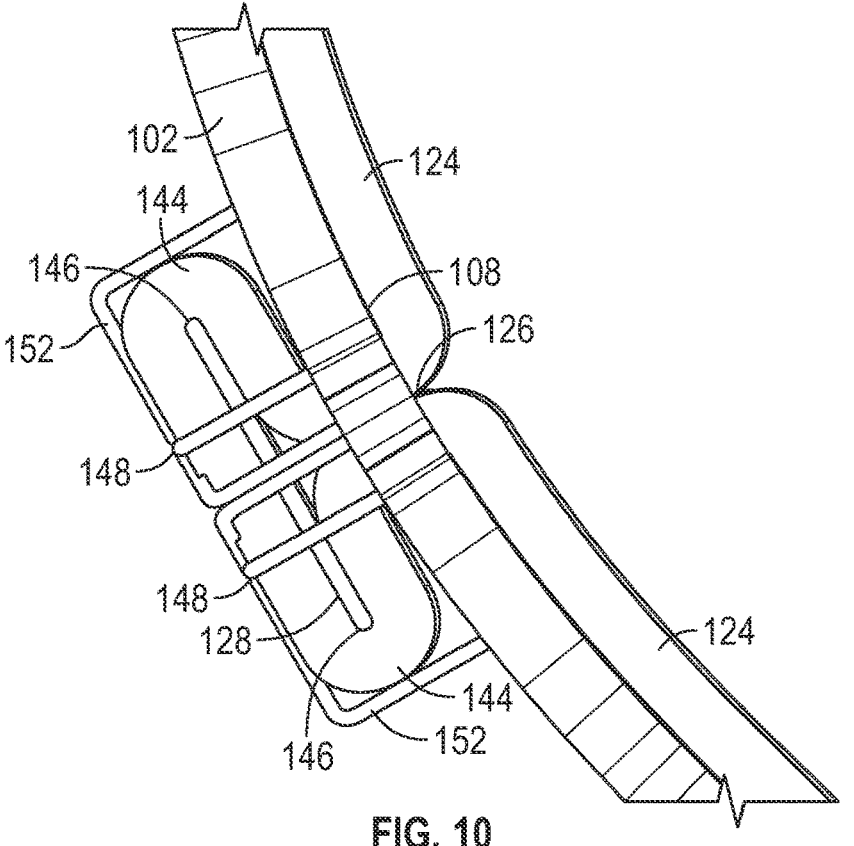
FIG. 10 is a top plan view of the prosthetic valve of FIG. 1.
Figure 11:
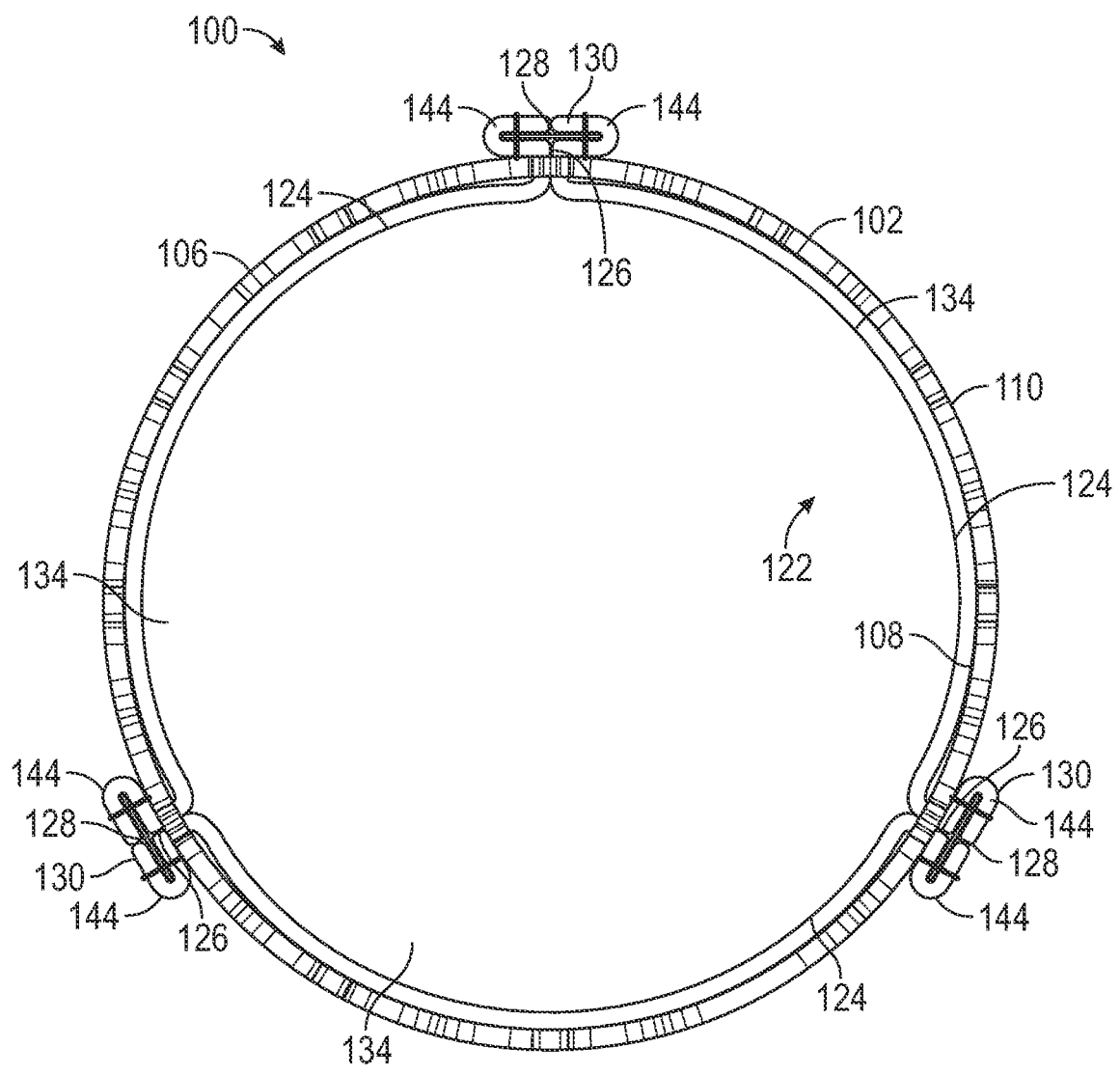
FIG. 11 is a top plan view of the prosthetic heart valve of FIG. 1, showing the valvular structure in an open configuration.
Figure 12:
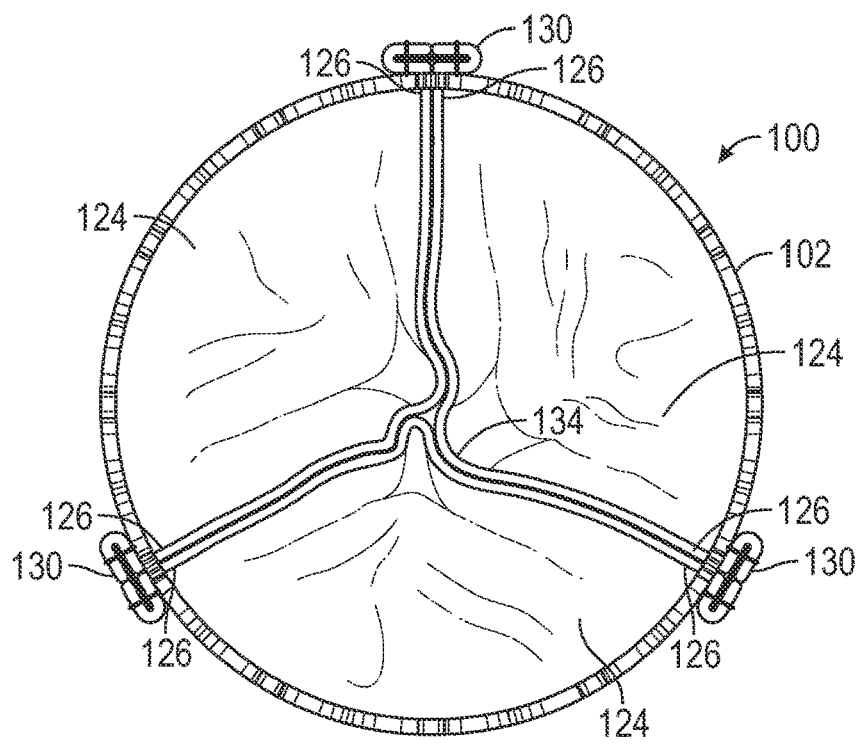
FIG. 12 is a top plan view of the prosthetic heart valve of FIG. 11, showing the valvular structure in a closed configuration.

As best shown in shown in FIG. 10, the placement of the commissure tab assemblies 130 on the outer surface 110 of the frame 102 allows the contact region 126 between adja-cent leaflets 124 to be located against or in very close proximity to the inner surface 108 of the frame 102. For each commissure assembly, the contact region 126 defines a bending axis around which the main bodies of the leaflets move during working cycles of the valve. This placement of the contact region 126 of each commissure tab assembly 130 at (or in close proximity to) the inner surface 108 maximizes the opening of the leaflets 124 by allowing the main bodies 143 and/or outflow edges 134 of the leaflets 124 to contact the inner surface 108 of the frame 102 when the leaflets 124 are in an open configuration. As such, when the valvular structure 122 is in an open state (e.g., during systole) the leaflets 124 open wider than generally permitted with known valves.

Typically, prosthetic valves can include one or more skirts or sealing members, such as an inner skirt mounted on the inner surface of the frame. These inner skirts often function as a way of protecting the leaflets against damage (e.g., abrasion) caused by contact with the frame when the pros-thetic valve is radially compressed and during working cycles of the prosthetic valve. However, abrasion commonly effecting the prosthetic leaflets can be negligible in smaller diameter valves (e.g., 20 mm or less). Referring to FIGS. 1 and 4, when the leaflets 124 open under the flow of blood, the leaflets 124 can be arranged circumferentially along the inner surface 108 of the frame 102 without an inner skirt between the leaflets 124 and the frame 102 due to the valve's 100 small diameter 138 (e.g., 20 mm or less). Consequently, and in conjunction with the placement of the commis sure tab assemblies 130, by omitting an inner skirt lining between the leaflets 124 and the inner surface 108 of the frame 102, the leaflets 124 can come in contact, or in close contact, with the frame 102, thereby allowing the leaflets to open wider than usually permitted.

In some embodiments, it may be further desirable to omit the inner skirt from the prosthetic valve 100 to prevent or minimize tissue ingrowth within the interior of the frame 102. Also, as depicted in FIGS. 1 and 3, it may also be desirable to omit any fabric components on or adjacent the commissure assemblies 130 to prevent or minimize tissue ingrowth that can initiate at the commissures and spread inward through the openings 120 of the frame. For example, tissue ingrowth extending into the interior of the frame 102 and on an inner skirt can inhibit full opening of the leaflets 124 during systole, increasing the pressure gradient across the valve. In some embodiments, the prosthetic valve 100 includes no fabric components within the interior of the frame 102, on the commissure tab assemblies 130, and/or at least in areas inside the frame that can come in contact with the moveable portions of the leaflets 124 to avoid tissue ingrowth at those areas of the prosthetic valve.

Figure 13:
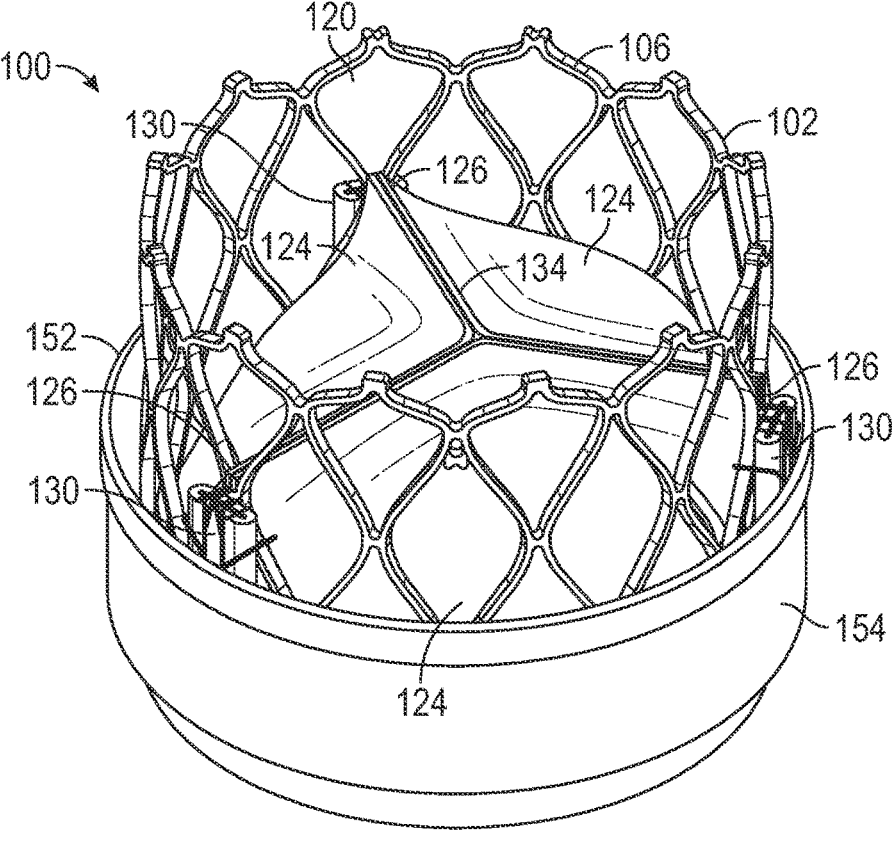
FIG. 13 is a perspective view of the prosthetic heart valve shown in a radially expanded state, having an outer skirt mounted on an outer surface of the prosthetic valve frame.
Figure 14:
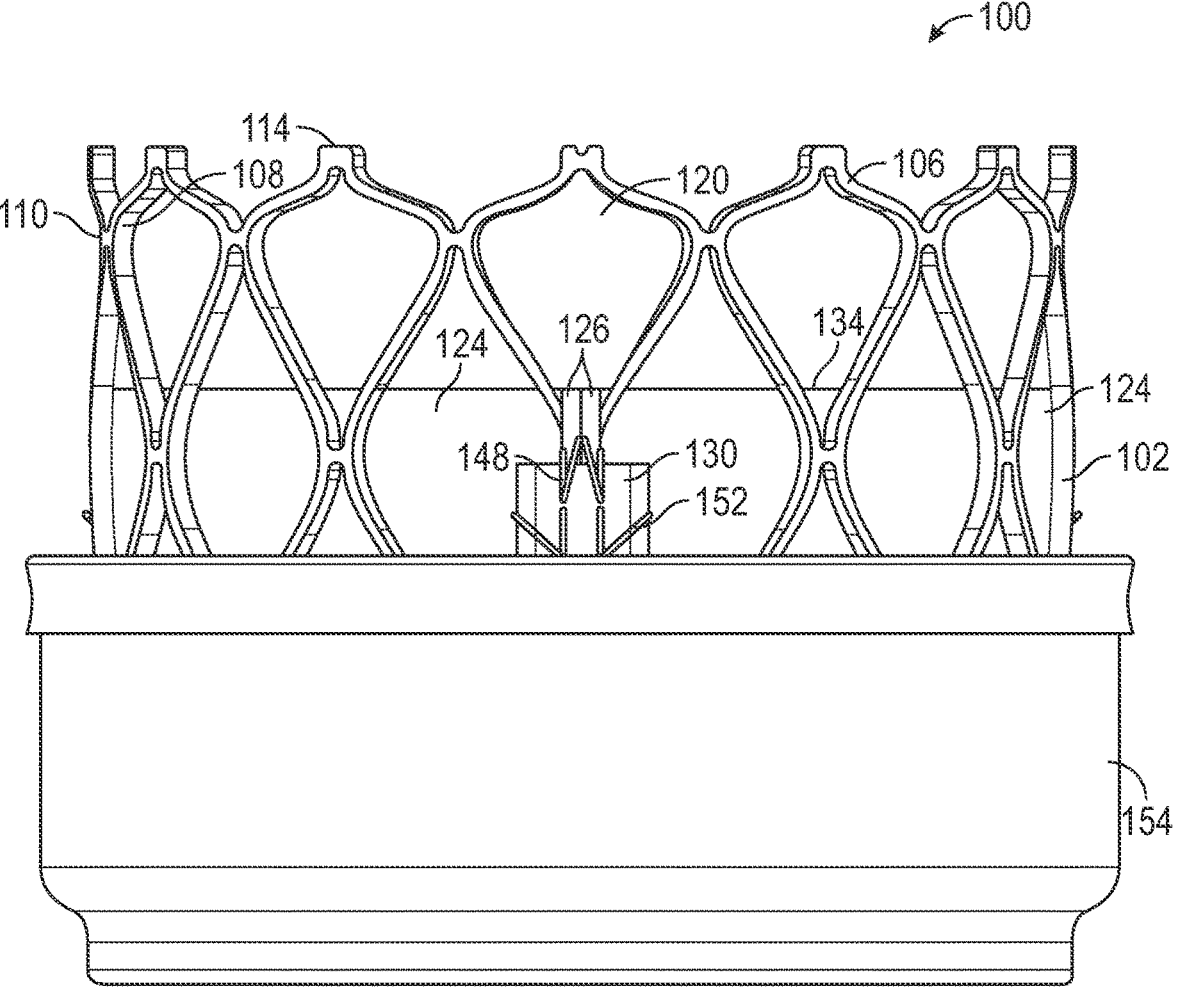
FIG. 14 is a side view of the prosthetic heart valve of FIG. 13.

As shown in FIGS. 13 and 14, the prosthetic valve 100 can also include an outer skirt 154 mounted on the outer surface 110 of the frame 102. In embodiments where an inner skirt or fabric is omitted from and/or on the frame 102 and commissure tab assemblies 130, the outer skirt 154 can function as a sealing member for the prosthetic valve 100 by sealing against the tissue of the native valve annulus and helping to reduce paravalvular leakage past the prosthetic valve. The outer skirt 154 can be formed from any of various suitable biocompatible materials, including any of various synthetic materials (e.g., PET) or natural tissue (e.g., pericardial tissue). The outer skirt 154 can be mounted to the frame 102 using sutures, an adhesive, welding, and/or other means for attaching the outer skirt 154 to the frame 102.

Figure 15:
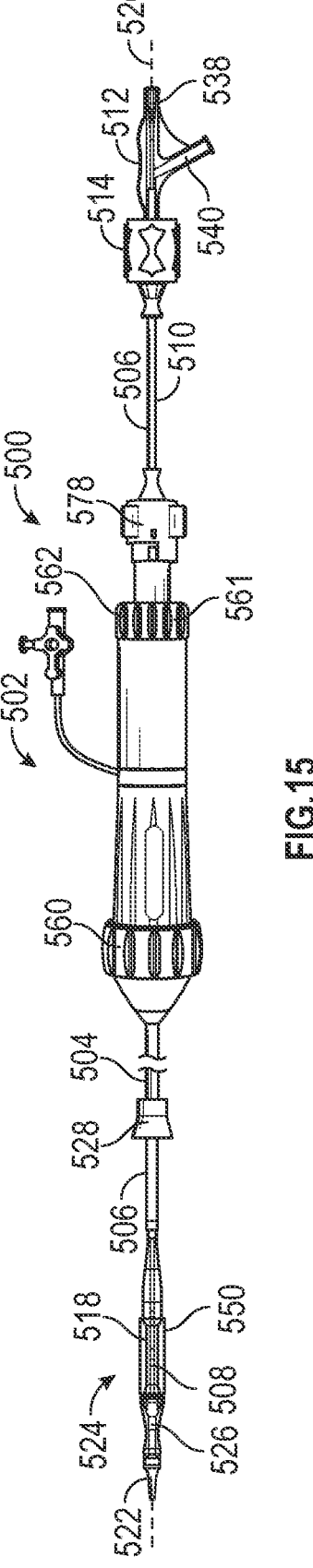
FIG. 15 is a side view of a delivery apparatus for a prosthetic heart valve, according to one embodiment.

FIG. 15 shows a delivery apparatus 500, according to an embodiment, that can be used to implant an expandable prosthetic heart valve (e.g., prosthetic heart valve 100 of FIG. 1 or any of the other prosthetic heart valves described herein). In some embodiments, the delivery apparatus 500 is specifically adapted for use in introducing a prosthetic valve into a heart.

The delivery apparatus 500 in the illustrated embodiment of FIG. 15 is a balloon catheter comprising a handle 502 and a steerable, outer shaft 504 extending distally from the handle 502. The delivery apparatus 500 can further comprise an intermediate shaft 506 (which also may be referred to as a balloon shaft) that extends proximally from the handle 502 and distally from the handle 502, the portion extending distally from the handle 502 also extending coaxially through the outer shaft 504. Additionally, the delivery apparatus 500 can further comprise an inner shaft 508 extending distally from the handle 502 coaxially through the intermediate shaft 506 and the outer shaft 504 and proximally from the handle 502 coaxially through the intermediate shaft 506.

The outer shaft 504 and the intermediate shaft 506 can be configured to translate (e.g., move) longitudinally, along a central longitudinal axis 520 of the delivery apparatus 500, relative to one another to facilitate delivery and positioning of a prosthetic valve at an implantation site in a patient's body.

The intermediate shaft 506 can include a proximal end portion 510 that extends proximally from a proximal end of the handle 502, to an adaptor 512. A rotatable knob 514 can be mounted on the proximal end portion 510 and can be configured to rotate the intermediate shaft 506 around the central longitudinal axis 520 and relative to the outer shaft 504.

The adaptor 512 can include a first port 538 configured to receive a guidewire therethrough and a second port 540 configured to receive fluid (e.g., inflation fluid) from a fluid source. The second port 540 can be fluidly coupled to an inner lumen of the intermediate shaft 506.

The intermediate shaft 506 can further include a distal end portion that extends distally beyond a distal end of the outer shaft 504 when a distal end of the outer shaft 504 is positioned away from an inflatable balloon 518 of the delivery apparatus 500. A distal end portion of the inner shaft 508 can extend distally beyond the distal end portion of the intermediate shaft 506.

The balloon 518 can be coupled to the distal end portion of the intermediate shaft 506.

In some embodiments, a distal end of the balloon 518 can be coupled to a distal end of the delivery apparatus 500, such as to a nose cone 522 (as shown in FIG. 15), or to an alternate component at the distal end of the delivery apparatus 500 (e.g., a distal shoulder). An intermediate portion of the balloon 518 can overlay a valve mounting portion 524 of a distal end portion of the delivery apparatus 500 and a distal end portion of the balloon 518 can overly a distal shoulder 526 of the delivery apparatus 500. The valve mounting portion 524 and the intermediate portion of the balloon 518 can be configured to receive a prosthetic heart valve in a radially compressed state. For example, as shown schematically in FIG. 15, a prosthetic heart valve 550 (which can be one of the prosthetic valves described herein) can be mounted around the balloon 518, at the valve mounting portion 524 of the delivery apparatus 500.

The balloon shoulder assembly, including the distal shoulder 526, is configured to maintain the prosthetic heart valve 550 (or other medical device) at a fixed position on the balloon 518 during delivery through the patient's vasculature.

The outer shaft 504 can include a distal tip portion 528 mounted on its distal end. The outer shaft 504 and the intermediate shaft 506 can be translated axially relative to one another to position the distal tip portion 528 adjacent to a proximal end of the valve mounting portion 524, when the prosthetic valve 550 is mounted in the radially compressed state on the valve mounting portion 524 (as shown in FIG. 15) and during delivery of the prosthetic valve to the target implantation site. As such, the distal tip portion 528 can be configured to resist movement of the prosthetic valve 550 relative to the balloon 518 proximally, in the axial direction, relative to the balloon 518, when the distal tip portion 528 is arranged adjacent to a proximal side of the valve mounting portion 524.

An annular space can be defined between an outer surface of the inner shaft 508 and an inner surface of the intermediate shaft 506 and can be configured to receive fluid from a fluid source via the second port 540 of the adaptor 512. The annular space can be fluidly coupled to a fluid passageway formed between the outer surface of the distal end portion of the inner shaft 508 and an inner surface of the balloon 518.

As such, fluid from the fluid source can flow to the fluid passageway from the annular space to inflate the balloon 518 and radially expand and deploy the prosthetic valve 550.

An inner lumen of the inner shaft can be configured to receive a guidewire therethrough, for navigating the distal end portion of the delivery apparatus 500 to the target implantation site.

The handle 502 can include a steering mechanism configured to adjust the curvature of the distal end portion of the delivery apparatus 500. In the illustrated embodiment, for example, the handle 502 includes an adjustment member, such as the illustrated rotatable knob 560, which in turn is operatively coupled to the proximal end portion of a pull wire. The pull wire can extend distally from the handle 502 through the outer shaft 504 and has a distal end portion affixed to the outer shaft 504 at or near the distal end of the outer shaft 504. Rotating the knob 560 can increase or decrease the tension in the pull wire, thereby adjusting the curvature of the distal end portion of the delivery apparatus 500. Further details on steering or flex mechanisms for the delivery apparatus can be found in U.S. Pat. No. 9,339,384, which is incorporated by reference herein.

The handle 502 can further include an adjustment mechanism 561 including an adjustment member, such as the illustrated rotatable knob 562, and an associated locking mechanism including another adjustment member, configured as a rotatable knob 578. The adjustment mechanism 561 is configured to adjust the axial position of the intermediate shaft 506 relative to the outer shaft 504 (e.g., for fine positioning at the implantation site). Further details on the delivery apparatus 500 can be found in U.S. Provisional Application Nos. 63/069,567 and 63/138,890, which are incorporated by reference herein.

General Considerations

It should be understood that the disclosed embodiments can be adapted for delivering and implanting prosthetic devices in any of the native annuluses of the heart (e.g., the aortic, pulmonary, mitral, and tricuspid annuluses), and can be used with any of various delivery devices for delivering the prosthetic valve using any of various delivery approaches (e.g., retrograde, antegrade, transseptal, transventricular, transatrial, etc.).

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone in various combinations and sub-combinations with one another. The methods, apparatus, and systems are not limited to any specific aspect or feature or combination thereof, nor do the disclosed embodiments require that any one or more specific advantages be present or problems be solved. The technologies from any example can be combined with the technologies described in any one or more of the other examples. In view of the many possible embodiments to which the principles of the disclosed technology may be applied, it should be recognized that the illustrated embodiments are only preferred examples and should not be taken as limiting the scope of the disclosed technology.

Although the operations of some of the disclosed embodiments are described in a particular sequential order for convenient presentation, it should be understood that this manner of description encompasses rearrangement, unless a particular ordering is required by specific language set forth herein. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used herein, with reference to the prosthetic heart valve and the transcatheter delivery system, "proximal" refers to a position, direction, or portion of a component that is closer to the user and a handle of the delivery system that is outside the patient, while "distal" refers to a position, direction, or portion of a component that is further away from the user and the handle and closer to the implantation site. The terms "longitudinal" and "axial" refer to an axis extending in the proximal and distal directions, unless otherwise expressly defined.

As used in the application and in the claims, the singular forms "a," "an," and "the" include the plural forms unless the context clearly dictates otherwise. Additionally, the term "includes" means "comprises." Further, the terms "coupled" and "connected" generally mean electrically, electromagnetically, and/or physically (e.g., mechanically or chemically) coupled or linked and does not exclude the presence of intermediate elements between the coupled or associated items absent specific contrary language.

Directions and other relative references (e.g., inner, outer, upper, lower, etc.) may be used to facilitate discussion of the drawings and principles herein, but are not intended to be limiting. For example, certain terms may be used such as "inside," "outside," "top," "down," "interior," "exterior," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" part can become a "lower" part simply by turning the object over. Nevertheless, it is still the same part and the object remains the same. As used herein, "and/or" means "and" or "or," as well as "and" and "or."

Additional Examples of the Disclosed Technology

In view of the above described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1: A prosthetic heart valve comprising: an expandable annular frame having an inflow end, an outflow end, an interior, an exterior, a plurality of openings, and a longitudinal axis; a plurality of commissure supports members outside of the frame; and a plurality of quadrilateral valve leaflets each having a main body having an inflow edge and an outflow edge, and a pair of opposing leaflet tabs extending from opposite sides of the main body, each leaflet tab being paired with an adjacent leaflet tab of an adjacent leaflet, each pair of leaflets tabs extending through a respective opening of the frame and coupled to one of the commissure supports to form a commissure tab assembly, wherein each commissure tab assembly is located on the exterior of the frame and the main body of each leaflet is located on the interior of the frame; wherein the inflow edges of the leaflets and the inflow end of the frame are aligned, and the outflow edges of the leaflets are axially offset from the outflow end of the frame along the longitudinal axis.

Example 2: The prosthetic heart valve of any example herein, particularly example 1, wherein each leaflet tab is wrapped circumferentially around a respective commissure support member.

Example 3: The prosthetic heart valve of any example herein, particularly any one of examples 1-2, wherein each leaflet tab forms a first fold extending radially outwardly from the main body of a respective leaflet, a second fold extending circumferentially along an inner surface of a respective commissure support member, and a third fold extending circumferentially along an outer surface of the commissure support member.

Example 4: The prosthetic heart valve of any example herein, particularly example 3, wherein the first folds of each pair of leaflet tabs extends through a respective opening of the frame.

Example 5: The prosthetic heart valve of any example herein, particularly any one of examples 3-4, wherein each leaflet tab is secured to a respective commissure support member with one or more sutures extending through the second fold of the leaflet tab, the commissure support member, and the third fold of the leaflet tab.

Example 6: The prosthetic heart valve of any example herein, particularly example 5, wherein each commissure support comprises plurality of apertures through which the one or more sutures extend.

Example 7: The prosthetic heart valve of any example herein, particularly any one of examples 1-6, wherein each leaflet tab has an outflow edge axially offset from the outflow edge of the main body of the leaflet and an inflow edge axially offset from the inflow edge of the main body of the leaflet.

Example 8: The prosthetic heart valve of any example herein, particularly any one of examples 1-7, wherein each commissure tab assembly is coupled to the outer surface of the frame by one or more sutures.

Example 9: The prosthetic heart valve of any example herein, particularly any one of examples 1-8, wherein for each commissure tab assembly, the commissure support member has a height that is greater than a height of a respective frame opening through which the pair of leaflet tabs extends.

Example 10: The prosthetic heart valve of any example herein, particularly any one of examples 1-9, wherein for each commissure tab assembly, the commissure support member has a width that is greater than a width of a respective frame opening through which the pair of leaflet tabs extends.

Example 11: The prosthetic heart valve of any example herein, particularly any one of examples 1-10, wherein the openings of the frame are defined by rows of angles struts of the frame.

Example 12: The prosthetic heart valve of any example herein, particularly example 11, wherein openings of the frame are arranged in circumferentially extending rows of openings, including a first row at the inflow end of the frame and a second row at the outflow end of the frame.

Example 13: The prosthetic heart valve of any example herein, particularly example 12, wherein for each row of openings, the openings have the same size.

Example 14: The prosthetic heart valve of any example herein, particularly any one of examples 12-13, wherein a majority of each opening of the second row is uncovered by the leaflets when the leaflets are in an open position.

Example 15: The prosthetic heart valve of any example herein, particularly any one of examples 1-14, further comprising an outer skirt having a first end located at the inflow end of the frame and a second end located between the inflow end and the outflow end of the frame, the outer skirt extending along the outer surface of the frame from the first end toward the second end.

Example 16: The prosthetic heart valve of any example herein, particularly any one of examples 1-15, wherein the frame has a diameter less than 23 millimeters and a height between 15 millimeters and 18 millimeters.

Example 17: The prosthetic heart valve of any example herein, particularly example 16, wherein the frame has a diameter of 20 millimeters or less.

Example 18: The prosthetic heart valve of any example herein, particularly any one of examples 1-17, wherein the leaflets have a height greater than or equal to 11 millimeters.

Example 19: The prosthetic heart valve of any example herein, particularly any one of examples 1-18, wherein the leaflets have a minimum height of 11 millimeters, and the frame has a diameter of 20 millimeters or less and a height between 15 millimeters and 18 millimeters.

Example 20: The prosthetic heart valve of any example herein, particularly any one of examples 1-19, wherein the frame has a diameter to height ratio between about 1.24 and about 1.34.

Example 21: The prosthetic heart valve of any example herein, particularly any one of examples 1-20, wherein the diameter of the frame and the height of the leaflets have a diameter to height ratio between about 1.61 and about 1.71.

Example 22: The prosthetic heart valve of any example herein, particularly any one of examples 1-21, wherein the height of the frame and height of the leaflets have a frame height to leaflet height ratio between about 1.24 and about 1.34.

Example 23: The prosthetic heart valve of any example herein, particularly any one of examples 1-22, wherein each opening of the frame between the outflow edge of the leaflets and the outflow end of the frame has a maximum width equal to or greater than 2 millimeters.

Example 24: A prosthetic heart valve comprising: an annular frame having an inflow end, an outflow end, a plurality of openings, and a longitudinal axis; a plurality of commissure support members each having an outer surface and an inner surface; and a plurality of valve leaflets each having a main body having an inflow edge and an outflow edge, and a pair of opposing leaflet tabs extending from opposite sides of the main body, each leaflet tab being paired with an adjacent leaflet tab of an adjacent leaflet, wherein each pair of leaflets tabs extends through a respective opening of the frame and is coupled to one of the commis sure supports outside of the frame to form a commissure tab assembly; wherein each leaflet tab forms a first fold extending radially outwardly from the main body of a respective leaflet through a respective opening of the frame, a second fold extending circumferentially between the inner surface of a respective support member and an exterior surface of the frame, and a third fold extending circumferentially along the outer surface of the support member.

Example 25: The prosthetic heart valve of any example herein, particularly example 24, wherein each of the leaflets is configured to open under fluid pressure such that the outflow edges of the leaflets contact the frame.

Example 26: The prosthetic heart valve of any example herein, particularly any one of examples 24-25, wherein each commissure support member comprises a rectangular plate with flat and parallel inner and outer surfaces.

Example 27: The prosthetic heart valve of any example herein, particularly any one of examples 24-26, wherein each leaflet tab is secured to a respective commissure support member with one or more sutures extending through the second fold of the leaflet tab, the commis sure support member, and the third fold of the leaflet tab.

Example 28: The prosthetic heart valve of any example herein, particularly example 27, wherein each commissure support comprises plurality of apertures through which the one or more sutures extend.

Example 29: The prosthetic heart valve of any example herein, particularly any one of examples 24-28, wherein for each commissure tab assembly, the commissure support member has a height that is greater than a height of a respective frame opening through which the pair of leaflet tabs extends.

Example 30: The prosthetic heart valve of any example herein, particularly any one of examples 24-29, further comprising an outer skirt having a first end located at the inflow end of the frame and a second end located between the inflow end and the outflow end of the frame, the outer skirt extending along the outer surface of the frame from the first end to the second end.

Example 31: The prosthetic heart valve of any example herein, particularly example 30, wherein the outer skirt partially covers the commissure tab assemblies.

Example 32: The prosthetic heart valve of any example herein, particularly any one of examples 24-31, wherein the inflow edges of the leaflets are coupled to the inflow end of the frame by one or more sutures extending through the leaflets and around struts of the frame that define the inflow end of the frame.

Example 33: The prosthetic heart valve of any example herein, particularly any one of examples 24-32, wherein the prosthetic heart valve is devoid of any fabric material inside of the frame.

Example 34: The prosthetic heart valve of any example herein, particularly any one of examples 24-33, wherein the commis sure assemblies are devoid of any fabric material.

Example 35: The prosthetic heart valve of any example herein, particularly any one of examples 24-34, wherein the outflow edges of the leaflets are axially offset from the outflow end of the frame along the longitudinal axis.

Example 36: The prosthetic heart valve of any example herein, particularly example 35, wherein the openings of the frame are arranged in circumferentially extending rows of openings, including a first row at the inflow end of the frame and a second row at the outflow end of the frame.

Example 37: The prosthetic heart valve of any example herein, particularly example 36, wherein the outflow edges of the leaflets are located upstream of a plane that is perpendicular to the longitudinal axis and bisects the openings of the second row of openings.

Example 38: The prosthetic heart valve of any example herein, particularly any one of examples 24-37, wherein the leaflets are quadrilateral in shape.

Example 39: The prosthetic heart valve of any example herein, particularly example 38, wherein each leaflet is rectangular in shape and has a width greater than a height.

Example 40: A prosthetic heart valve comprising: an expandable annular frame having an inflow end, an outflow end, an interior, an exterior, a plurality of openings, and a longitudinal axis; a plurality of commis sure supports members outside of the frame; and a plurality of valve leaflets each having a main body having an inflow edge and an outflow edge, and a pair of opposing leaflet tabs extending from opposite sides of the main body, each leaflet tab being paired with an adjacent leaflet tab of an adjacent leaflet, each pair of leaflets tabs extending through a respective opening of the frame and coupled to one of the commissure supports to form a commissure tab assembly, wherein each commissure tab assembly is located on the exterior of the frame and the main body of each leaflet is located on the interior of the frame; wherein for each commis sure tab assembly, the commissure support member has a height that is greater than a height of a respective frame opening through which the pair of leaflet tabs extends.

Example 41: The prosthetic heart valve of any example herein, particularly example 40, wherein each leaflet tab forms a first fold extending radially outwardly from the main body of a respective leaflet, a second fold extending circumferentially along an inner surface of a respective commissure support member, and a third fold extending circumferentially along an outer surface of the commissure support member.

Example 42: The prosthetic heart valve of any example herein, particularly example 41, wherein the first folds of each pair of leaflet tabs extends through a respective opening of the frame.

Example 43: The prosthetic heart valve of any example herein, particularly any one of examples 41-42, wherein each leaflet tab is secured to a respective commissure support member with one or more sutures extending through the second fold of the leaflet tab, the commis sure support member, and the third fold of the leaflet tab.

Example 44: The prosthetic heart valve of any example herein, particularly example 43, wherein each commissure support comprises plurality of apertures through which the one or more sutures extend.

Example 45: The prosthetic heart valve of any example herein, particularly any one of examples 40-44, wherein the inflow edges of the leaflets and the inflow end of the frame are aligned, and the outflow edges of the leaflets are axially offset from the outflow end of the frame along the longitudinal axis.

Example 46: The prosthetic heart valve of any example herein, particularly any one of examples 40-45, wherein the frame comprises a row of openings bounded by a row of struts of the frame that define the outlet end of the frame and the outflow edges of the leaflets are upstream of a majority of each opening in the row.

Example 47: The prosthetic heart valve of any example herein, particularly any one of examples 40-46, wherein the frame has a diameter less than 23 millimeters and a height between 15 millimeters and 18 millimeters.

Example 48: The prosthetic heart valve of any example herein, particularly example 47, wherein the frame has a diameter of 20 millimeters or less.

Example 49: The prosthetic heart valve of any example herein, particularly any one of examples 40-48, wherein the leaflets have a height greater than or equal to 11 millimeters.

Example 50: The prosthetic heart valve of any example herein, particularly any one of examples 40-49, wherein the leaflets have a minimum height of 11 millimeters, and the frame has a diameter of 20 millimeters or less and a height between 15 millimeters and 18 millimeters.

Example 51: The prosthetic heart valve of any example herein, particularly any one of examples 40-50, wherein the leaflets are quadrilateral in shape.

Example 52: The prosthetic heart valve of any example herein, particularly example 51, wherein each leaflet is rectangular in shape and has a width greater than a height.

Example 53: A leaflet assembly for a prosthetic heart valve comprising: a plurality of valve leaflets, each leaflet comprising a main body having an inflow edge and an outflow edge, and opposing commissure tabs extending from opposite sides of the main body; and a plurality of commissure support members, each having a pair of opposing faces; wherein each commis sure tab is paired with an adjacent commissure tab of an adjacent leaflet and for each pair of commissure tabs, the commis sure tabs are wrapped partially around and coupled to the opposing faces of one of the support members to form a commissure assembly.

Example 54: The leaflet assembly of any example herein, particularly example 53, wherein each commissure tab forms a first fold extending radially outwardly from the main body of a respective leaflet, a second fold extending circumferentially along an inner surface of a respective commissure support member, and a third fold extending circumferentially along an outer surface of the commissure support member.

Example 55: The leaflet assembly of any example herein, particularly example 54, wherein each commissure tab is secured to a respective commissure support member with one or more sutures extending through the second fold of the commissure tab, the commis sure support member, and the third fold of the commissure tab.

Example 56: The leaflet assembly of any example herein, particularly example 55, wherein each commissure support comprises plurality of apertures through which the one or more sutures extend.

Example 57: The leaflet assembly of any example herein, particularly example 56, wherein the apertures are arranged in a two-column configuration.

Example 58: The leaflet assembly of any example herein, particularly example 56, wherein the apertures are in a single column configuration.

Example 59: The leaflet assembly of any example herein, particularly any one of examples 53-58, wherein the valve leaflets are made of discrete pieces of pericardium.

Example 60: The leaflet assembly of any example herein, particularly any one of examples 53-58, wherein the valve leaflets are sections of a unitary piece of pericardium.

Example 61: The leaflet assembly of any example herein, particularly any one of examples 53-60, wherein the leaflets are quadrilateral in shape.

Example 62: The leaflet assembly of any example herein, particularly any one of examples 61, wherein each leaflet is rectangular in shape and has a width greater than a height.

Example 63: A method for assembling a prosthetic heart valve, comprising: forming a leaflet assembly from a plurality of leaflets, each leaflet comprising opposing commissure tabs, wherein the leaflet assembly is formed by pairing a commissure tab of each leaflet with an adjacent commissure tab of an adjacent leaflet and connecting each pair of commissure tabs to a commissure support member to form a respective commissure assembly of the leaflet assembly; positioning the leaflet assembly within an interior of an expandable annular frame, wherein the frame defines a plurality of openings; and inserting each of the commis sure assemblies through a respective opening of the frame so as to position the commis sure assemblies an exterior of the frame.

Example 64: The method of any example herein, particularly example 63, wherein inserting each of the commissure assemblies of the leaflet assembly through the respective opening of the frame, further comprises: deforming each of the commissure assemblies relative to main bodies of the leaflets from a first position to a second position such that the commissure assemblies are in a deformed orientation in the second position; inserting each of the commissure assemblies in the second position through the respective opening of the frame such that each commis sure support member is positioned entirely on the exterior of the frame; and after inserting each commissure assembly through the respective opening, moving each of the commissure assemblies from the second position back to the first position.

Example 65: The method of any example herein, particularly any one of examples 63-64, wherein positioning the leaflet assembly within the interior of the frame further comprises: aligning an inflow edge of the leaflet assembly with an inflow end of the frame; and positioning an outflow edge of the leaflet assembly between the inflow end and an outflow end of the frame.

Example 66: The method of any example herein, particularly example 65, further comprising suturing the inflow edges of the leaflets to struts of the frame at the inflow end of the frame.

Example 67: The method of any example herein, particularly any one of examples 63-66, wherein the leaflets are quadrilateral in shape.

Example 68: The method of any example herein, particularly example 67, wherein each leaflet is rectangular in shape and has a width greater than a height.

Example 69: The method of any example herein, particularly any one of examples 63-68, wherein connecting each pair of commissure tabs to a commissure support member to form a respective commissure assembly comprises: folding each commis sure tab of the pair to form a first fold against a first side of a commissure support member and a second fold against a second side of the commis sure support member; and suturing the first and second folds to the commissure support member.

Example 70: The method of any example herein, particularly any one of examples 63-69, wherein each commissure support member has a dimension that is greater than a dimension of a respective frame opening through which the commissure support member was inserted to prevent the commissure assembly from being pulled inwardly into the frame after the commissure assembly is positioned outside of the frame.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. I therefore claim as my invention all that comes within the scope and spirit of these claims.

The invention claimed is:

1. A prosthetic heart valve comprising:
an expandable annular frame having an inflow end, an outflow end, an interior, an exterior, a plurality of openings, and a longitudinal axis;
a plurality of commissure support members outside of the frame; and
a plurality of quadrilateral valve leaflets each having a main body having an inflow edge, an outflow edge, and a pair of opposing leaflet tabs extending from opposite sides of the main body, each leaflet tab being paired with an adjacent leaflet tab of an adjacent leaflet, each pair of leaflet tabs extending through a respective opening of the frame and coupled to one of the commissure support members to form a commissure tab assembly, wherein each commissure tab assembly is located on the exterior of the frame and the main body of each leaflet is located on the interior of the frame;
wherein the inflow edges of the leaflets and the inflow end of the frame are aligned, the outflow edges of the leaflets are axially offset from the outflow end of the frame along the longitudinal axis, and for each commissure tab assembly, the commissure support member has a width greater than a width of a respective frame opening through which the pair of leaflet tabs extends.

2. The prosthetic heart valve of claim 1, wherein each leaflet tab is wrapped circumferentially around a respective commissure support member.

3. The prosthetic heart valve of claim 1, wherein each leaflet tab forms a first fold extending radially outwardly from the main body of a respective leaflet, a second fold extending circumferentially along an inner surface of a respective commissure support member, and a third fold extending circumferentially along an outer surface of the commissure support member.

4. The prosthetic heart valve of claim 3, wherein the first folds of each pair of leaflet tabs extends through a respective opening of the frame.

5. The prosthetic heart valve of claim 3, wherein each leaflet tab is secured to a respective commissure support member with one or more sutures extending through the second fold of the leaflet tab, the commissure support member, and the third fold of the leaflet tab.

6. The prosthetic heart valve of claim 1, wherein each leaflet tab has an outflow edge axially offset from the outflow edge of the main body of the leaflet and an inflow edge axially offset from the inflow edge of the main body of the leaflet.

7. The prosthetic heart valve of claim 1, wherein each commissure tab assembly is coupled to the outer surface of the frame by one or more sutures.

8. The prosthetic heart valve of claim 1, wherein for each commissure tab assembly, the commissure support member has a height greater than a height of a respective frame opening through which the pair of leaflet tabs extends.

9. The prosthetic heart valve of claim 1, wherein the openings of the frame are arranged in circumferentially extending rows of openings, including a first row at the inflow end of the frame and a second row at the outflow end of the frame.

10. The prosthetic heart valve of claim 9, wherein the majority of the openings of the second row are uncovered by the leaflets when the leaflets are in an open position.

11. A prosthetic heart valve comprising:
an annular frame having an inflow end, an outflow end, and a plurality of openings;
a plurality of commissure support members each having an outer surface and an inner surface; and
a plurality of valve leaflets each having a main body having an inflow edge, an outflow edge, and a pair of opposing leaflet tabs extending from opposite sides of the main body, each leaflet tab being paired with an adjacent leaflet tab of an adjacent leaflet, wherein each pair of leaflet tabs extends through a respective opening of the frame and is coupled to one of the commissure supports outside of the frame to form a commissure tab assembly;
wherein each leaflet tab forms a first fold extending radially outwardly from the main body of a respective leaflet through a respective opening of the frame, a second fold extending circumferentially between the inner surface of a respective support member and an exterior surface of the frame, and a third fold extending circumferentially along the outer surface of the support member.

12. The prosthetic heart valve of claim 11, wherein each leaflet is configured to open under fluid pressure such that the outflow edges of the leaflets contact the frame.

13. The prosthetic heart valve of claim 11, wherein each commissure support member comprises a rectangular plate with flat and parallel inner and outer surfaces.

14. The prosthetic heart valve of claim 11, wherein each leaflet tab is secured to a respective commissure support member with one or more sutures extending through the second fold of the leaflet tab, the commissure support member, and the third fold of the leaflet tab.

15. The prosthetic heart valve of claim 14, wherein each commissure support comprises plurality of apertures through which the one or more sutures extend.

16. The prosthetic heart valve of claim 11, further comprising an outer skirt having a first end located at the inflow end of the frame and a second end located between the inflow end and the outflow end of the frame, the outer skirt extending along the outer surface of the frame from the first end to the second end.

17. The prosthetic heart valve of claim 16, wherein the outer skirt partially covers the commissure tab assemblies.

18. The prosthetic heart valve of claim 11, wherein the prosthetic heart valve is devoid of any fabric material inside of the frame.

19. The prosthetic heart valve of claim 11, wherein the commissure assemblies are devoid of any fabric material.

20. The prosthetic heart valve of claim 1, wherein the commissure support members are made of metal.

21. A prosthetic heart valve comprising:

an expandable annular frame having an inflow end, an outflow end, an interior, an exterior, a plurality of openings, and a longitudinal axis;

a plurality of commissure support members outside of the frame; and a plurality of quadrilateral valve leaflets each having a main body having an inflow edge, an outflow edge, and a pair of opposing leaflet tabs extending from opposite sides of the main body, each leaflet tab being paired with an adjacent leaflet tab of an adjacent leaflet, each pair of leaflet tabs extending through a respective opening of the frame and coupled to one of the commissure support members to form a commissure tab assembly, wherein each commissure tab assembly is located on the exterior of the frame and the main body of each leaflet is located on the interior of the frame;

wherein the inflow edges of the leaflets and the inflow end of the frame are aligned, the outflow edges of the leaflets are axially offset from the outflow end of the frame along the longitudinal axis, and for each commissure tab assembly, the commissure support member has a height greater than a height of a respective frame opening through which the pair of leaflet tabs extends.

\* \* \* \* \*